US006473645B1

(12) United States Patent
Levine

(10) Patent No.: US 6,473,645 B1
(45) Date of Patent: Oct. 29, 2002

(54) SYSTEM AND METHOD FOR PROGRAMMABLY CONTROLLING ELECTRODE ACTIVATION SEQUENCE IN A MULTI-SITE CARDIAC STIMULATION DEVICE

(75) Inventor: Paul A. Levine, Santa Clarita, CA (US)

(73) Assignee: Pacesetter, Inc., Sylmar, CA (US)

( * ) Notice: Subject to any disclaimer, the term of this patent is extended or adjusted under 35 U.S.C. 154(b) by 0 days.

(21) Appl. No.: 09/904,056

(22) Filed: Jul. 11, 2001

Related U.S. Application Data

(62) Division of application No. 09/835,006, filed on Apr. 12, 2001.

(51) Int. Cl.$^7$ ............................................... A61N 1/362
(52) U.S. Cl. ............................................................ 607/9
(58) Field of Search ...................................... 607/4–26

(56) References Cited

U.S. PATENT DOCUMENTS

| | | | |
|---|---|---|---|
| 4,628,934 A | 12/1986 | Pohndorf et al. | ............ 128/419 |
| 4,991,583 A | 2/1991 | Silvian | .................. 128/419 PG |

(List continued on next page.)

FOREIGN PATENT DOCUMENTS

| | | | | |
|---|---|---|---|---|
| NL | WO99/30777 | 6/1999 | .......... | A61N/1/368 |

OTHER PUBLICATIONS

Cazeau, S. et al., "Four Chamber Pacing in Dilated Cardiomyopathy," PACE 1994 (Nov. Part II, vol. 17) pp 1974–1979.

Misier A., MD, PhD., et al., "Multisite or Alternate Site Pacing for the Prevention of Atrial Fibrillation," American Journal of Cardiology., Mar. 11, 1999 vol. 83(5B) pp 237D–240D.

Berder V., et al. "La Resynchronisation Atriale Permanente Dans Les Blocs Inter–Auriculaires De Haunt Degre: Aspects Electrophysiologiques Et Hemodynamiques", Stimucoeur 1993. Tome 21. No. 3, pp 157–163.

Saksena S. MD, et al. "Prevention of Recurrent Atrial Fibrillation with Chronic Dual–Site Right Atrial Pacing", JACC 1996 (9: vol. 28 No. 3) pp 687–694.

Levine, P. et al., "Cross–Stimulation: the Unexpected Stimulation of the Unpaced Chamber" PACE 1985 vol. 8 (Jul.–Aug.) pp 600–606.

*Primary Examiner*—Scott M. Getzow

(57) ABSTRACT

An implant able multi-chamber cardiac stimulation device includes flexibly programmable electrode sensing configurations, and is capable of precisely controlling the stimulation sequence between multiple sites. The stimulation device provides a plurality of connection ports that allow independent connection of each electrical lead associated with a particular stimulation site in the heart. Each connection port further provides a unique terminal for making electrical contact with only one electrode such that no two electrodes are required to be electrically coupled. Furthermore, each electrode, whether residing on a unipolar, bipolar or multipolar lead, may be selectively connected or disconnected through programmable switching circuitry that determines the electrode configurations to be used for sensing and for stimulating at each stimulation site. The stimulation device possesses unique sensing and output configurations associated with each stimulation site, such that depolarizations occurring at each stimulation site can be detected independently of events occurring at other sites within the heart, and such that each site can be stimulated independently of other sites or on a precisely timed basis triggered by events occurring at other sites. The stimulation device is further capable of uniquely programming coupling intervals for precisely controlling the activation sequence of stimulated sites. Coupling intervals are selected so as to provide optimal hemodynamic benefit to the patient.

43 Claims, 10 Drawing Sheets

U.S. PATENT DOCUMENTS

| | | | |
|---|---|---|---|
| 5,411,528 A | 5/1995 | Miller et al. | 607/5 |
| 5,423,873 A | 6/1995 | Neubauer et al. | 607/68 |
| 5,441,518 A | 8/1995 | Adams et al. | 607/5 |
| 5,466,254 A | 11/1995 | Helland | 607/123 |
| 5,476,483 A | 12/1995 | Bornzin et al. | 607/17 |
| 5,501,702 A | 3/1996 | Plicchi et al. | 607/20 |
| 5,514,161 A | 5/1996 | Limousin | 607/9 |
| 5,593,430 A | 1/1997 | Renger | 607/18 |
| 5,720,518 A | 2/1998 | Harrison | 297/214 |
| 5,720,768 A | 2/1998 | Verboven-Nelissen | 607/9 |
| 5,792,203 A | 8/1998 | Schroeppel | 607/30 |
| 5,800,465 A | 9/1998 | Thompson et al. | 607/9 |
| 5,800,471 A | 9/1998 | Baumann | 607/25 |
| 5,843,141 A | 12/1998 | Bischoff et al. | 607/37 |
| 5,899,930 A | 5/1999 | Flynn et al. | 607/37 |
| 5,902,324 A | 5/1999 | Thompson et al. | 607/9 |
| 6,085,119 A | 7/2000 | Scheiner et al. | 607/122 |

SYSTEM AND METHOD FOR PROGRAMMABLY CONTROLLING ELECTRODE ACTIVATION SEQUENCE IN A MULTI-SITE CARDIAC STIMULATION DEVICE

CROSS-REFERENCE TO RELATED APPLICATIONS

This application is a division of copending U.S. application Ser. No. 09/835,006, filed Apr. 12, 2001, titled "System and Method for Automatically Selecting Electrode Polarity During Sensing and Stimulation."

FIELD OF THE INVENTION

This invention relates generally to programmable cardiac stimulating devices. More specifically, the present invention is directed to an implant able stimulation device and associated method for controlling the electrode sensing and stimulation configurations and the activation sequence in a multi-chamber cardiac stimulation device using noninvasive programming techniques.

BACKGROUND OF THE INVENTION

In a normal human heart, the sinus node, generally located near the junction of the superior vena cava and the right atrium, constitutes the primary natural pacemaker initiating rhythmic electrical excitation of the heart chambers. The cardiac impulse arising from the sinus node is transmitted to the two atrial chambers, causing a depolarization known as a P-wave and the resulting atrial chamber contractions. The excitation pulse is further transmitted to and through the ventricles via the atrioventricular (A-V) node and a ventricular conduction system causing a depolarization known as an R-wave and the resulting ventricular chamber contractions.

Disruption of this natural pacemaking and conduction system as a result of aging or disease can be successfully treated by artificial cardiac pacing using implant able cardiac stimulation devices, including pacemakers and implant able defibrillators, which deliver rhythmic electrical pulses or other anti-arrhythmia therapies to the heart at a desired energy and rate. One or more heart chambers may be electrically stimulated depending on the location and severity of the conduction disorder.

Cardiac pacemakers conventionally stimulate a heart chamber by applying current pulses to cardiac tissues via two electrodes, a cathode and an anode. Standard pacing leads are available in either of two configurations, unipolar leads or bipolar leads, depending on the arrangement of the electrodes of a particular lead. A unipolar pacing lead contains a single electrode, normally the cathode, which extends pervenously distal from the pacemaker in an insulating enclosure until it is adjacent to the tip of the lead where the insulation is terminated to provide for electrical contact of the cathode with the heart tissue. The anode provides a return path for the pacing electrical circuit. For a unipolar lead, the anode is the pacemaker case.

A bipolar lead contains two electrodes within an insulating sheath, an anode that extends distal from the pacemaker to a position adjacent to, but spaced from, the electrode tip, and a cathode that also extends distal from the pacemaker, but terminates a short distance distal of the anode, at the lead tip. The anode commonly takes the form of a ring having greater surface area than the cathode tip. An insulating barrier separates the cathode and anode of a bipolar lead. In present-day pacemakers, circuits for pacing and sensing, which determine tip, ring and case electrode connections, are provided. Thus, the pacemakers can be programmed via telemetry for either bipolar or unipolar operation with respect to either sensing or pacing operations.

A single-chamber pacemaker delivers pacing pulses to one chamber of the heart, either one atrium or one ventricle, via either a unipolar or bipolar electrode. Single-chamber pacemakers can operate in either a triggered mode or a demand mode. In a triggered mode, a stimulation pulse is delivered to the desired heart chamber at the end of a defined time-out interval to cause depolarization of the heart tissue (myocardium) and it's contraction. The stimulating pulse must be of sufficient energy to cause depolarization of the heart chamber, a condition known as "capture." The lowest pulse energy required to achieve capture is termed "threshold." The pacemaker also delivers a stimulation pulse in response to a sensed event arising from that chamber when operating in a triggered mode.

When operating in a demand mode, sensing and detection circuitry allow for the pacemaker to detect if an intrinsic cardiac depolarization, either an R-wave or a P-wave, has occurred within the defined time-out interval. If an intrinsic depolarization is not detected, a pacing pulse is delivered at the end of the time-out interval. However, if an intrinsic depolarization is detected, the pacing pulse output is inhibited to allow the natural heart rhythm to preside. The difference between a triggered and demand mode of operation is the response of the pacemaker to a detected native event.

Dual chamber pacemakers are now commonly available and can provide either trigger or demand type pacing in both an atrial chamber and a ventricular chamber, typically the right atrium and the right ventricle. Both unipolar or bipolar dual chamber pacemakers exist in which a unipolar or bipolar lead extends from an atrial channel of the dual chamber device to the desired atrium (e.g. the right atrium), and a separate unipolar or bipolar lead extends from a ventricular channel to the corresponding ventricle (e.g. the right ventricle). In dual chamber, demand-type pacemakers, commonly referred to as DDD pacemakers, each atrial and ventricular channel includes a sense amplifier to detect cardiac activity in the respective chamber and an output circuit for delivering stimulation pulses to the respective chamber.

If an intrinsic atrial depolarization signal (a P-wave) is not detected by the atrial channel, a stimulating pulse will be delivered to depolarize the atrium and cause contraction. Following either a detected P-wave or an atrial pacing pulse, the ventricular channel attempts to detect a depolarization signal in the ventricle, known as an R-wave. If no R-wave is detected within a defined atrial-ventricular interval (AV interval or delay), a stimulation pulse is delivered to the ventricle to cause ventricular contraction. In this way, rhythmic dual chamber pacing is achieved by coordinating the delivery of ventricular output in response to a sensed or paced atrial event.

Mounting clinical evidence supports the evolution of more complex cardiac stimulating devices capable of stimulating three or even all four heart chambers to stabilize arrhythmias or to re-synchronize heart chamber contractions (Ref: Cazeau S. et al., "Four chamber pacing in dilated cardiomyopathy," Pacing Clin. Electrophsyiol 1994 17(11 Pt 2):1974–9). Stimulation of multiple sites within a heart chamber has also been found effective in controlling arrhythmogenic depolarizations (Ref: Ramdat-Misier A., et al., "Multisite or alternate site pacing for the prevention of atrial fibrillation," Am. J. Cardiol., 1999 11;83(5b):237D–240D).

In order to achieve multi-chamber or multi-site stimulation in a clinical setting, conventional dual-chamber pacemakers have now been used in conjunction with adapters that couple together two leads going to different pacing sites or heart chambers. Reference is made to U.S. Pat. No. 5,514,161 to Limousin in which a triple chamber cardiac pacemaker, with the right and left atrial combined with a right ventricular lead, is described. Cazeau et al. (Pacing Clin. Electrophsyiol 1994 17(11 Pt 2):1974–9) describe a four chamber pacing system in which unipolar right and left atrial leads are connected via a bifurcated bipolar adapter to the atrial port of a bipolar dual chamber pacemaker. Likewise, unipolar right and left ventricular leads are connected via a bifurcated bipolar adapter to the ventricular channel. The left chamber leads were connected to the anode terminals and the right chamber leads were connected to the cathode terminals of the dual chamber device. In this way, simultaneous bi-atrial or simultaneous bi-ventricular pacing is achieved via bipolar stimulation but with several limitations.

Firstly, this configuration of bipolar stimulation is distinctly different from a conventional bipolar lead configuration wherein both the cathode and anode are located a short distance apart, approximately one centimeter, on the same lead. In the bi-chamber pacing configuration described above, the anode and cathode are in fact located on two different leads positioned in two different locations, several centimeters apart. In addition, since the tip electrode of one lead is forced to be the anode, and this has a significantly smaller surface area than the anode of a classic bipolar lead, the relative resistance or impedance is higher with this lead system. In such a bipolar, bi-chamber pacing configuration, the threshold energy is likely to be relatively higher than in conventional bipolar stimulation in part because of the higher impedance of the electrode system. In addition, the electrode used for stimulation in the left heart chamber is usually within the coronary sinus or a cardiac vein, not making direct contact with the myocardium. As such, the energy needed to accommodate bi-chamber stimulation will usually be higher than that which is commonly required for single chamber stimulation using bipolar leads.

A potential risk that exists when higher output settings are used, as may be needed to ensure bi-chamber stimulation, is cross-chamber capture, also known as cross-stimulation (Ref: Levine P A, et al., Cross-stimulation: the unexpected stimulation of the unpaced chamber, PACE 1985: 8: 600–606). If bi-atrial stimulation is delivered in a bipolar configuration across one electrode located in the right atrium and another electrode located in the left atrium, which in actuality is the coronary sinus which lies between the left atrium and left ventricle, the stimulation energy could conceivably be high enough to inadvertently capture one or both ventricles simultaneously. Such cross-chamber capture is a highly undesirable situation in that the upper and lower chambers would contract against each other causing severe cardiac output perturbation. This is also likely to occur with bipolar bi-ventricular stimulation with respect to cross-stimulation of the atrial chambers if the left ventricular lead located within a cardiac vein is in close anatomic proximity to the left atrium and high outputs are required to assure capture.

Another limitation of the multi-chamber stimulation systems described above is that simultaneous stimulation of left and right chambers, as required when two leads are coupled together by one adapter, is not always necessary nor desirable. For example, in some patients conduction between the two atria may be compromised, however the pacemaking function of the sinus node in the right atrium may still be normal. Hence, detection of an intrinsic depolarization in the right atrium could be used to trigger delivery of a pacing pulse in the left atrium. Since an intrinsic depolarization has occurred in one chamber, simultaneous stimulation of both chambers in this situation is unnecessary.

In another example, when inter-atrial or inter-ventricular conduction is intact, stimulation in one chamber may be conducted naturally to depolarize the second chamber. A stimulation pulse delivered in one chamber, using the minimum energy required to depolarize that chamber, will be conducted to the opposing chamber thus depolarizing both chambers. In this case, stimulation of both chambers simultaneously would be wasteful of battery energy.

Another limitation is that, in the presence of an inter-atrial or inter-ventricular conduction defect, one may want to control the interval between a sensed or paced event in one chamber and delivery of a stimulation pulse to the other chamber. If pacing is required in both chambers, the control of the sequence of the stimulation pulse delivery to each chamber, rather than the simultaneous delivery of stimulation pulses, may be desirable in order to achieve a specific activation sequence that has hemodynamic benefit.

Yet another limitation is that, once implanted, the designation of cathode and anode assignments is fixed and cannot be reassigned in order to determine the polarity that results in the lowest stimulation thresholds, to achieve a desired directionality of the stimulation delivery or to obtain the optimal sequencing of stimulation and/or sensing to optimize hemodynamic function. Typically, the electrode in the right chamber is connected to the cathode terminal and the electrode in the left chamber is connected to the anode terminal. In other cases, the electrode in the left chamber is connected to the cathode terminal while the right chamber electrode is connected to the anode. In some patients, a lower stimulation threshold or an improved excitation pattern or perhaps even hemodynamic benefit might be achieved by reversing the cathode and anode locations yet this cannot be done without operative intervention.

In the first generation of multi-chamber devices, an adapter was required to connect multiple leads to a conventional dual chamber device, a requirement that adds cost and time to the implant procedure. Adapters can be cumbersome and an additional site for potential lead breakage or discontinuity, essentially adding bulk and a "weak link" to the implanted system. In certain current devices, adapters are no longer required. The connection between leads is hardwired internally in the connector block coupling the ventricular leads to the ventricular channel and the atrial leads to the atrial channel. While this design advantageously eliminates the need for adapters, the hardwire connections preclude the potential to non-invasively adjust the polarity orientation. This also prevents introducing separate timing between stimulation pulses delivered to each chamber or responding with any programmable delays to a sensed event by delivery of an output pulse to the other chamber.

To address some of these limitations, Verboven-Nelissen proposes a method and apparatus that includes a multiple-chamber electrode arrangement having at least two electrodes placed to sense and/or pace different chambers or areas of the heart. Reference is made to U.S. Pat. No. 5,720,518. The proposed method involves switching from a bipolar to a unipolar configuration during sensing for determining the origination site of a detected depolarization signal. If the signal is determined to have arisen from the SA node in the right atrium, a conduction interval is applied to allow the cardiac signal to properly propagate to the other heart chambers. If no cardiac signal is detected in another cardiac chamber, for example, the left atrium, then pacing is initiated in that chamber at the end of the conduction interval. In this example, the interval is equal to the inter-atrial conduction time (i.e. the time required for a P-wave cardiac signal to propagate from right atrium to left atrium). However the inter-atrial conduction time may vary over time and the time for an excitation pulse to propagate from the right chamber to the left chamber may be different than the propagation time from the left chamber to the right chamber. In addition, the conduction time from the right atrium to the left atrium may vary from that required to go from the left atrium to the right atrium. Depending on the site of origin of the detected depolarization, it may be hemodynamically beneficial to control the coupling interval between the detected depolarization and the triggered output to the other chamber. U.S. Pat. No. 5,720,518 does not address the ability to control the interval between detection and stimulation within the atria or ventricles in the setting of multisite stimulation.

Reference is also made to U.S. Pat. No. 5,902,324 to Thompson et al. in which a multi-channel pacing system having two, three or four pacing channels, each including a sense amplifier and pace output pulse generator, is described. A pacing pulse or detection of a spontaneous depolarization in one of the right or left heart chambers is followed by a short conduction delay window. A pacing pulse that would otherwise be delivered at the termination of the conduction delay window in the opposing heart chamber is inhibited if the conducted depolarization wave is sensed within the conduction delay window. While the duration of the conduction delay window can be programmed, no method is provided by which to select the optimal interval between chamber depolarizations.

Patients with marked hemodynamic abnormalities may benefit from multi-site or multi-chamber pacing that controls the activation sequence of the heart chambers. Precise control of the activation sequence may improve the coordination of heart chamber contractions resulting in more effective filling and ejection of blood from the heart. Patients with hemodynamic abnormalities often have conduction defects due to dilation of the heart or other causes. Yet, even in patients with intact conduction, precise control of the timing and synchronicity of heart chamber contractions may provide hemodynamic benefit.

There remains an unmet need, therefore, for a multi-chamber or multi-site cardiac stimulation device that allows independent stimulation and sensing at multiple sites within the heart as well as flexible selection of stimulation sequence and timing intervals between these stimulation sites. It would thus be desirable to provide a multisite or multichamber cardiac stimulation device having independent sensing and output circuitry for each pacing site. It would further be desirable to allow flexible selection of sensing and stimulation polarity for each stimulation site, including the designation of cathode and anode assignment during bi-chamber stimulation. Further, it would be desirable to provide flexible programming of the stimulation sequence and timing intervals associated with multisite or multichamber pacing. Different timing intervals should be advantageously selectable depending on the origination site of a detected depolarization wave or a desired directionality of depolarization in order to achieve optimal hemodynamic or electrophysiological benefit for the patient.

SUMMARY OF THE INVENTION

The present invention addresses this need by providing an implant able multichamber or multisite cardiac stimulation device in which the electrode configurations for sensing and stimulation are flexibly programmable, and the stimulation sequence between multiple sites can be precisely controlled.

One aspect of the present invention is to provide a plurality of connection ports, preferably two through four connection ports, that allow independent connection to the stimulation device of each electrical lead associated with a particular stimulation site in the heart. Each connection port further provides a unique terminal for making electrical contact with only one electrode such that no two electrodes are required to be electrically coupled. Furthermore, each electrode, whether residing on a unipolar, bipolar or multi-polar lead, may be selectively connected or disconnected through programmable switching circuitry that determines the electrode configurations to be used for sensing and for stimulating at each stimulation site.

Another aspect of the present invention is a unique sensing circuit associated with each stimulation site such that depolarizations occurring at each stimulation site can be detected independently of events occurring at other sites within the heart. This independent sensing advantageously allows the location of a detected depolarization to be recognized by the stimulation device. The desired electrodes to be used for sensing in a specific heart chamber or at a specific site within a heart chamber are connected to the input of the sensing circuit via programmable switching circuitry.

Still another aspect of the present invention is a unique output circuit associated with each stimulation site such that each site can be stimulated independently of other sites or on a precisely timed basis triggered by events occurring at other sites. The electrodes used for stimulation at a specific site may be different than those used for sensing at the same site.

Yet another aspect of the present invention is the ability to program unique coupling intervals for precisely controlling the activation sequence of stimulated sites. Coupling intervals may be defined in relation to the originating location of a detected depolarization or in relation to stimulus delivery at another location. Coupling intervals are advantageously selected in a way that provides optimal hemodynamic benefit to the patient by overcoming various conduction disorders or improving coordination of heart chambers in patients suffering from heart failure. One embodiment of the present invention includes a method for automatically determining the optimal coupling intervals and adjusting the programmed settings based on measurements related to the hemodynamic state of the heart.

BRIEF DESCRIPTION OF THE DRAWINGS

Further features and advantages of the present invention may be more readily understood by reference to the following description taken in conjunction with the accompanying drawings, in which.

DETAILED DESCRIPTION OF THE INVENTION

The following description is of a best mode presently contemplated for practicing the invention. This description is not to be taken in a limiting sense but is made merely for the purpose of describing the general principles of the invention. The scope of the invention should be ascertained with reference to the issued claims. In the description of the invention that follows, like numerals or reference designators will be used to refer to like parts or elements throughout.

The present invention relates to a cardiac stimulation device capable of delivering precisely ordered stimulation pulses to multiple chambers of the heart, referred to herein as multi-chamber stimulation, or to multiple sites within a chamber of the heart, referred to herein as multi-site stimulation. As used herein, the shape of the stimulation pulses is not limited to an exact square or rectangular shape, but may assume any one of a plurality of shapes which is adequate for the delivery of an energy packet or stimulus.

The stimulation device is intended for use in patients suffering from hemodynamic dysfunction, which may or may not be accompanied by conduction disorders. Precisely controlled stimulation at multiple sites or in multiple chambers is provided to intentionally make use of the pacing function of the heart in order to improve cardiac hemodynamics by re-coordinating heart chamber contractions and/or preventing arrhythmogenic depolarizations from occurring. Thus, the cardiac stimulation device is capable of delivering at least low-voltage stimulation pulses to multiple stimulation sites for providing pacing therapy, and may include high-voltage stimulation shocks for providing cardioversion therapy and defibrillation therapy.

Figure 1:
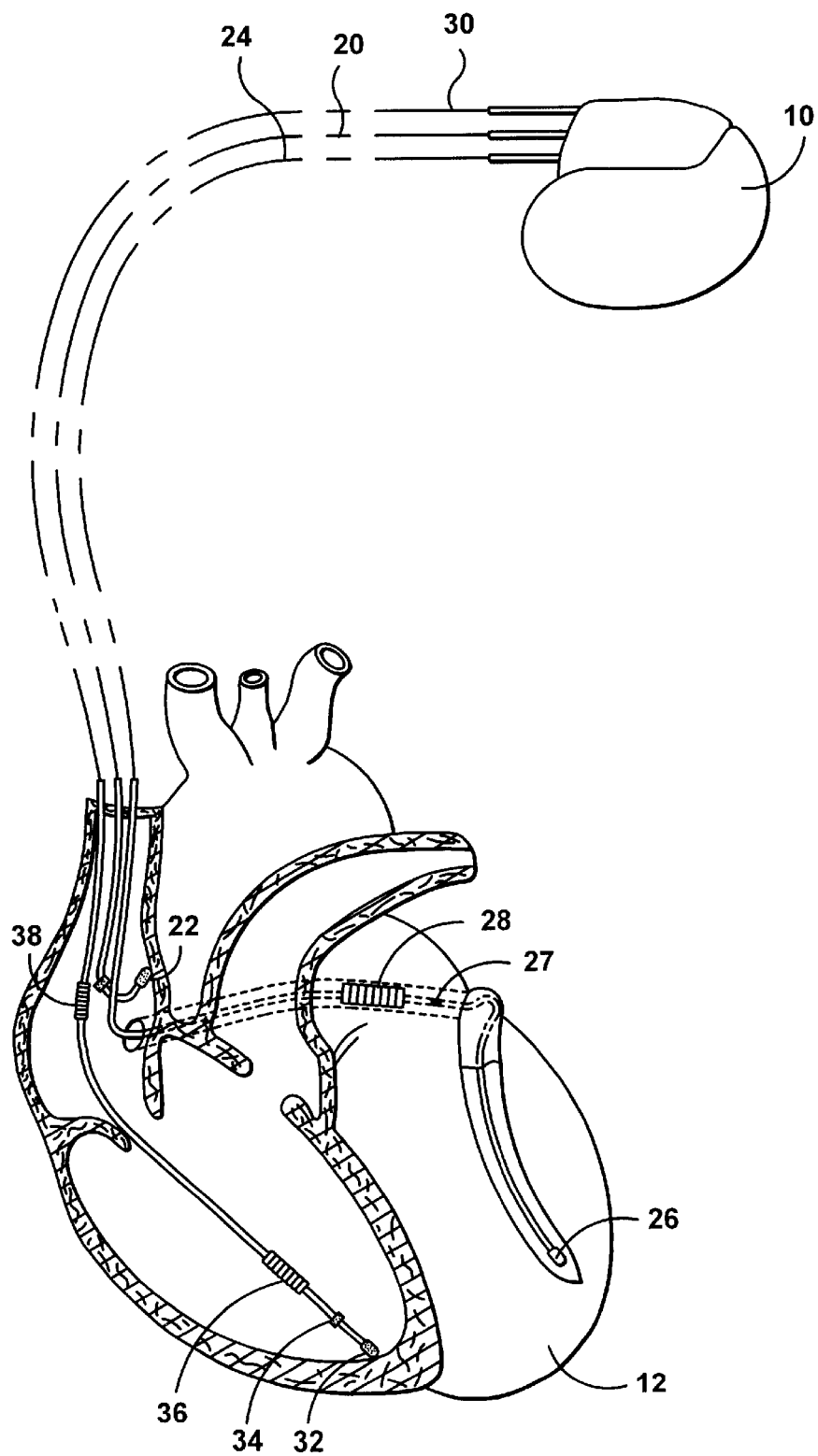
FIG. 1 is a simplified, partly cutaway view illustrating an implant able stimulation device in electrical communication with at least three leads implanted into a patient's heart for delivering multi-chamber stimulation and shock therapy.

FIG. 1 illustrates a stimulation device 10 in electrical communication with a patient's heart 12 by way of three leads 20, 24 and suitable for delivering multi-chamber stimulation and shock therapy. To sense right atrial cardiac signals and to provide right atrial chamber stimulation therapy, the stimulation device 10 is coupled to an implant able right atrial lead 20 having at least an atrial tip electrode 22, which typically is implanted in the patient's right atrial appendage.

To sense left atrial and/or left ventricular cardiac signals and to provide left-chamber pacing therapy, the stimulation device 10 is coupled to a "coronary sinus" lead 24 designed for placement in the "coronary sinus region" via the coronary sinus os so as to place a distal electrode adjacent to the left ventricle and additional electrode(s) adjacent to the left atrium. As used herein, the phrase "coronary sinus region" refers to the vasculature of the left ventricle, including any portion of the coronary sinus, great cardiac vein, left marginal vein, left posterior ventricular vein, middle cardiac vein, and/or small cardiac vein or any other cardiac vein accessible by the coronary sinus. It could also be an epicardial lead placed at the time of thoracotomy or thoracoscopy.

Accordingly, the coronary sinus lead 24 is designed to receive atrial and/or ventricular cardiac signals and to deliver: left ventricular pacing therapy using at least a left ventricular tip electrode 26, left atrial pacing therapy using at least a left atrial ring electrode 27, and shocking therapy using at least a left atrial coil electrode 28. For a more detailed description of a coronary sinus lead, refer to U.S. patent application Ser. No. 09/196,898, titled "A Self-Anchoring Coronary Sinus Lead" (Pianca et. al), and U.S. Pat. No. 5,466,254, titled "Coronary Sinus Lead with Atrial Sensing Capability" (Helland) that are incorporated herein by reference.

The stimulation device 10 is also shown in electrical communication with the patient's heart 12 by way of an implant able right ventricular lead 30 having, in this embodiment, a right ventricular tip electrode 32, a right ventricular ring electrode 34, a right ventricular (RV) coil electrode 36, and an SVC coil electrode 38. Typically, the right ventricular lead 30 is transvenously inserted into the heart 12 so as to place the right ventricular tip electrode 32 in the right ventricular apex so that the RV coil electrode 36 will be positioned in the right ventricle and the SVC coil electrode 38 will be positioned in the superior vena cava.

Accordingly, the right ventricular lead 30 is capable of receiving cardiac signals, and delivering stimulation in the form of pacing and shock therapy to the right ventricle.

Figure 2:
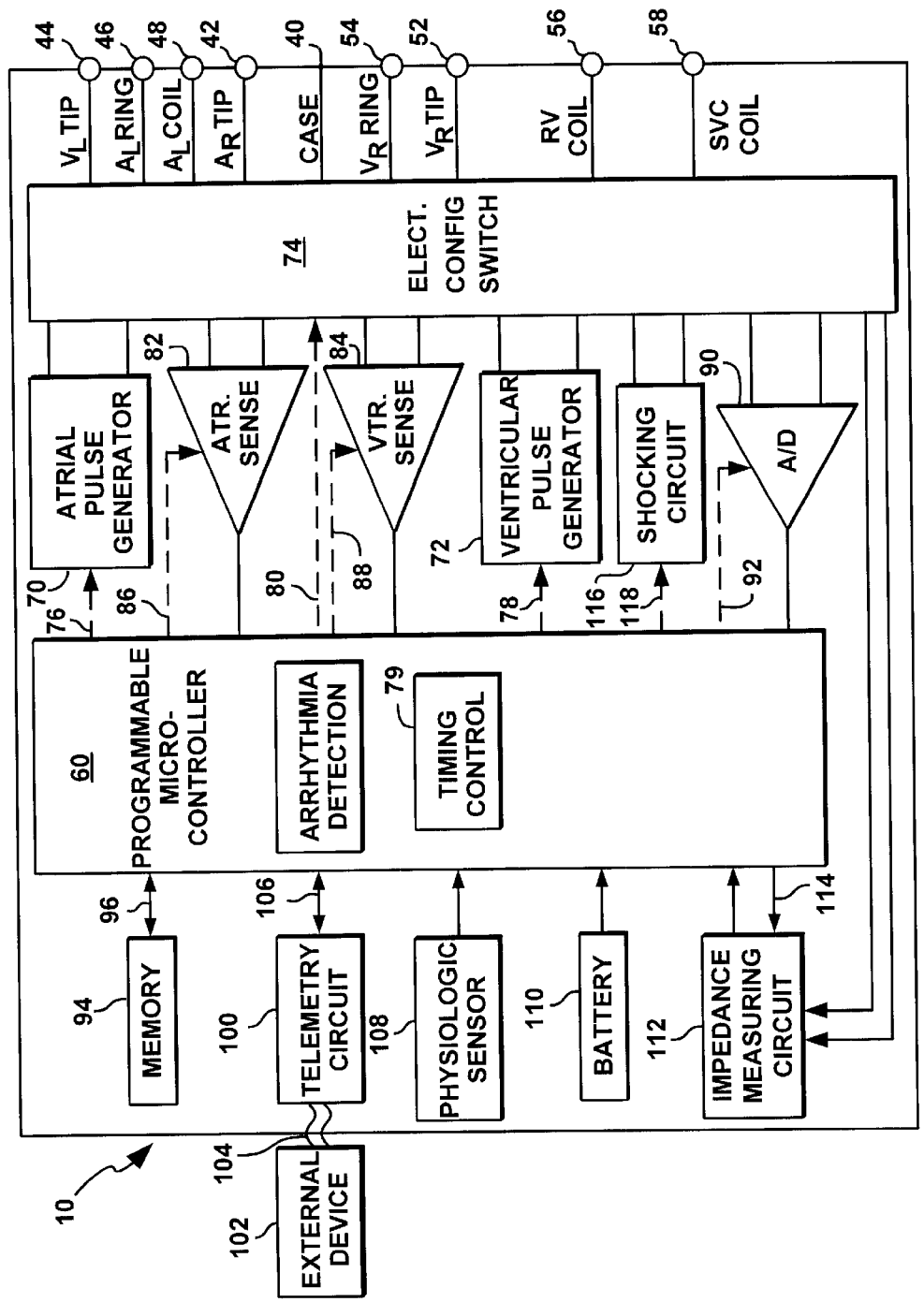
FIG. 2 is a functional block diagram of the multi-chamber implant able stimulation device of FIG. 1, illustrating the basic elements that provide pacing stimulation, cardioversion, and defibrillation in four chambers of the heart.

FIG. 2 illustrates a simplified block diagram of the multi-chamber implant able stimulation device 10, which is capable of treating both fast and slow arrhythmias with stimulation therapy, including cardioversion, defibrillation, and pacing stimulation. While a particular multi-chamber device is shown, this is for illustration purposes only, and one of skill in the art could readily duplicate, eliminate or disable the appropriate circuitry in any desired combination to provide a device capable of treating the appropriate chamber(s) with cardioversion, defibrillation and/or pacing stimulation.

The stimulation device 10 includes a housing 40 which is often referred to as "can", "case" or "case electrode", and which may be programmably selected to act as the return electrode for all "unipolar" modes. The housing 40 may further be used as a return electrode alone or in combination with one or more coil electrodes 28, 36, or 38, for shocking purposes. The housing 40 further includes a connector having a plurality of terminals, 42, 44, 46, 48, 52, 54, 56, and 58 (shown schematically and, for convenience, the names of the electrodes to which they are connected are shown next to the terminals). In accordance with the present invention, the connector will provide a unique connection port for each lead in communication with the heart so as to avoid the necessity of adapters. Furthermore, the connector will provide a unique terminal for electrical connection to each electrode(s) associated with each stimulation site within the heart 12. In this way, coupling of more than one stimulation site using adaptors, or hardwiring between terminals inside the connector, is avoided allowing independent stimulation and sensing at each stimulation site.

As such, in the embodiment of FIG. 2, the connector includes at least a right atrial tip terminal 42 adapted for connection to the atrial ($A_R$) tip electrode 22 in order to achieve right atrial sensing and pacing.

To achieve left chamber sensing, pacing and/or shocking, the connector includes at least a left ventricular ($V_L$) tip terminal 44, a left atrial ($A_L$) ring terminal 46, and a left ventricular ($V_L$) shocking terminal (coil) 48, which are adapted for connection to the left ventricular tip electrode 26, the left atrial ring electrode 27, and the left atrial coil electrode 28, respectively.

To support right ventricular sensing, pacing and/or shocking, the connector further includes a right ventricular ($V_R$) tip terminal 52, a right ventricular ($V_R$) ring terminal 54, a right ventricular (RV) shocking terminal (coil) 56, and an SVC shocking terminal (coil) 58, which are adapted for connection to the right ventricular tip electrode 32, right ventricular ring electrode 34, the RV coil electrode 36, and the SVC coil electrode 38, respectively. Thus, the embodiment of FIG. 1 includes one connection port for the right atrial lead 20 and two bipolar, high-voltage connection ports for the right ventricular lead 30 and the coronary sinus lead 24, allowing sensing and stimulation in all four chambers of the heart.

In alternative embodiments, the stimulation device 10 may include a multi-port connector capable of accommodating any combination of three, four or more uni-polar, bi-polar or multi-polar leads. The arrangement and type of leads used may vary depending on the type of stimulation therapy to be delivered and individual patient need. In a preferred embodiment, to be described later in conjunction with FIG. 3, four bipolar connection ports are provided to accommodate a programmable selection of unipolar, bipolar or combination stimulation and sensing in any or all four chambers of the heart, or at four sites within the heart 12.

At the core of the stimulation device 10 is a programmable microcontroller 60 that controls the various modes of stimulation therapy. As is well known in the art, the microcontroller 60 typically includes a microprocessor, or equivalent control circuitry, designed specifically for controlling the delivery of stimulation therapy, and may further include RAM or ROM memory, logic and timing circuitry, state machine circuitry, and I/O circuitry. Typically, the microcontroller 60 includes the ability to process or monitor input signals (data) as controlled by a program code stored in a designated block of memory. The details of the design and operation of the microcontroller 60 are not critical to the present invention. Rather, any suitable microcontroller 60 may be used that carries out the functions described herein. The use of microprocessor-based control circuits for performing timing and data analysis functions are well known in the art.

As shown in FIG. 2, an atrial pulse generator 70 and a ventricular pulse generator 72 generate pacing stimulation pulses for delivery by the right atrial lead 20, the right ventricular lead 30 and/or the coronary sinus lead 24, via the switch bank 74. It is understood that in order to provide stimulation therapy in each of the four chambers of the heart, or at multiple sites within one or more chambers, the atrial pulse generator 70 and the ventricular pulse generator 72 include dedicated, independent pulse generators, multiplexed pulse generators, or shared pulse generators. However, in order to provide independent stimulation at each stimulation site, atrial pulse generator 70 and ventricular pulse generator 72 include independent output circuits for each stimulation site that allow delivery of unique stimulation pulses to each site.

The atrial pulse generator 70 in FIG. 2 thus includes a right atrial output circuit for delivering stimulation pulses to the right atrium via right atrial lead 20, and further includes a left atrial output circuit for delivering stimulation pulses to the left atrium via coronary sinus lead 24. The ventricular pulse generator 72 includes a right ventricular output circuit for delivering stimulation pulses to the right ventricle via right ventricular lead 30, and further includes a left ventricular output circuit for delivering stimulation pulses to the left ventricle via the coronary sinus lead 24. The atrial pulse generator 70 and the ventricular pulse generator 72 are controlled by the microcontroller 60 via appropriate control signals 76 and 78, respectively, to trigger or inhibit the stimulation pulses.

The microcontroller 60 further includes timing control circuitry 79 which is used to control the timing of such stimulation pulses (e.g. pacing rate, atrio-ventricular (AV) delay, interatrial conduction (A-A) delay, or interventricular conduction (V-V) delay, etc.), as well as to keep track of the timing of refractory periods, PVARP intervals, noise detection windows, evoked response windows, alert intervals, marker channel timing, etc.

In accordance with one embodiment of the present invention, the timing control circuitry 79 is also used to control coupling intervals, which precisely control the stimulation sequence during multi-chamber or multi-site stimulation. For example, the interatrial conduction (A-A) delay may be determined by programmable selection of coupling intervals defined according to whether an intrinsic atrial depolarization is first sensed in the right atrium or in the left atrium. A right-to-left atrial coupling interval may be programmed to control the time between a right atrial detected event (P-wave) and the delivery of a left atrial stimulation pulse. A different left-to-right atrial coupling interval may be programmed to control the time between a left atrial detected P-wave and right atrial stimulation pulse delivery.

Furthermore, different coupling intervals may be defined in relation to paced events than detected events. Hence, the coupling interval between a right atrial paced event and a left atrial paced event may be different than the coupling interval between a right atrial detected event (intrinsic P-wave) and a left atrial paced event. In other words, for each stimulation site, a unique coupling interval between it and all other stimulation sites may be defined in relation to both paced events and detected events occurring at that site. Details regarding the application of coupling intervals as provided by the present invention will be described later in conjunction with FIGS. 5 through 10.

The switch bank 74 includes a plurality of switches for connecting the desired electrodes to the appropriate I/O circuits, thereby providing complete electrode programmability. Accordingly, the switch bank 74, in response to a control signal 80 from the microcontroller 60, determines the polarity of the stimulation pulses (e.g. unipolar, bipolar, combined manner, etc.) by selectively closing the appropriate combination of switches (not shown).

In addition to providing programmable stimulation polarity, the stimulation device 10 includes the programmable polar assignments of each electrode during bipolar or unipolar stimulation. For example, bi-ventricular stimulation may be provided in a combined manner between the right ventricular tip electrode 32 and left ventricular tip electrode 26 by connecting these two tip electrodes to ventricular pulse generator 72 via switch bank 74.

The stimulation device 10 provides the programmable assignment of cathode and anode poles in the following stimulation configuration. The left ventricular tip electrode 26 may be selected as the cathode with the right ventricular tip electrode 32 selected as the anode, to achieve one directionality and stimulation threshold. Alternatively, the left ventricular tip electrode 26 may be selected as the anode and the right ventricular tip electrode 32 may be selected as the cathode, to achieve a different directionality and stimulation threshold. In this way, the selection of cathode and anode assignments during bi-atrial or bi-ventricle stimulation, or within a chamber during multisite stimulation, may be tailored to meet the individual patient's need.

In some patients it may be advantageous to provide anodal stimulation rather than cathodal stimulation. Hence, it is one feature of the present invention to further allow assignment of the active electrode used in unipolar stimulation to be the anode with the housing 40 assigned as the cathode. For example, unipolar anodal stimulation of the right ventricle may be achieved by designating the right ventricular ring electrode 54 as the anode and the housing 40 as the cathode.

The programmable designation of electrode poles is preferably accomplished via electronic switching devices controlled by logic gates receiving high or low signals under the control of microprocessor 60. For details regarding a switching circuitry that may be used for providing programmable selection of stimulation and sensing electrode configurations, refer to U.S. Pat. No. 4,991,583 to Silvian, hereby incorporated herein by reference.

Atrial sensing circuit 82 and ventricular sensing circuit 84 may also be selectively coupled to the right atrial lead 20, coronary sinus lead 24, and the right ventricular lead 30, through the switch bank 74, for detecting the presence of cardiac activity in each of the four chambers of the heart. In order to detect events occurring within each chamber or at each stimulation site independently, the atrial and ventricular sensing circuits 82 and 84 include dedicated independent sense amplifiers associated with each stimulation site within the heart 12. As used herein, each of the atrial sensing circuit 82 and the ventricular sensing circuit 84 includes a discriminator, which is a circuit that senses and can indicate or discriminate the origin of a cardiac signal in each of the cardiac chambers.

The inputs to each sense amplifier are programmable and may be selected in any combination of available electrode terminals in order to provide independent unipolar or bipolar sensing at each stimulation site. In this way, a detected atrial event may be distinguished as being a right atrial event or a left atrial event. Likewise, a detected ventricular event may be distinguished as a right ventricular event or a left ventricular event.

If the stimulation device 10 is being used for multisite stimulation within a chamber of the heart, one electrode might be positioned in the upper area of the chamber and a second electrode might be positioned in a lower area of the same chamber or any two distinct locations within that chamber. Unique sensing circuitry for each electrode allows discrimination of a detected event as occurring in either the upper area or the lower area of the chamber. The stimulation response provided by the device 10 may then be determined based on the location of a detected event.

Additionally, combination sensing for bi-atrial or bi-ventricular sensing during multichamber stimulation or combipolar sensing within a single chamber during multisite stimulation may be selected by programming the appropriate inputs to the individual sense amplifiers. The switch bank 74 determines the "sensing polarity" of the cardiac signal by selectively closing the appropriate switches. In this way, the clinician may program the sensing polarity independent of the stimulation polarity.

Each of the atrial sensing circuit 82 or the ventricular sensing circuit 84 preferably employs one or more low power, precision amplifiers with programmable gain and/or automatic gain control, bandpass filtering, and a threshold detection circuit, to selectively sense the cardiac signal of interest. The automatic gain control enables the stimulation device 10 to deal effectively with the difficult problem of sensing the low amplitude signal characteristics of atrial or ventricular fibrillation. The outputs of the atrial and ventricular sensing circuits 82 and 84 are connected to the microcontroller 60 for triggering or inhibiting the atrial and ventricular pulse generators 70 and 72, respectively, in a demand fashion, in response to the absence or presence of cardiac activity, respectively, in the appropriate chambers of the heart.

One feature of the present invention is to provide precise control of the activation sequence of the stimulation sites. To this end, the stimulation device 10 may act only in a trigger mode thereby gaining complete control of the heart rhythm in an attempt to provide a more hemodynamically effective contraction sequence of the heart chambers than that produced by the natural heart rhythm.

Preferably, the stimulation device 10 operates in a trigger mode in controlling the timing of contraction at all the stimulation sites. Alternatively, it may operate in a demand mode in delivering or inhibiting stimulation pulses to at least one site, and may operate in a trigger mode in delivering stimulation pulses to all other stimulation sites. For example, atrial pulse generator 70 may be inhibited from delivering a right atrial stimulation pulse when atrial sensing circuit 82 detects an intrinsic P-wave in the right atrium within a given escape interval. However, this detection may cause microcontroller 60 to trigger atrial pulse generator 70 and ventricular pulse generator 72 to deliver stimulation pulses at prescribed intervals of time to the left atrium and the right and left ventricles, respectively, regardless of any events detected in these chambers. In this way, the activation sequence of all four heart chambers is precisely controlled by the natural pacemaking activity of the sinus node. Hence, in the present invention, the pacing mode of stimulation device 10, that is demand or trigger mode, for each stimulation site is preferably programmable.

If the cardiac stimulation device 10 is also intended for delivering cardioversion and defibrillation therapy, arrhythmia detection by the stimulation device 10 utilizes the atrial and ventricular sensing circuits 82 and 84 to sense cardiac signals, for determining whether a rhythm is physiologic or pathologic. As used herein "sensing" is reserved for the noting of an electrical signal, and "detection" is the processing of these sensed signals and noting the presence of an arrhythmia. The timing intervals between sensed events (e.g. P-waves, R-waves, and depolarization signals associated with fibrillation which are sometimes referred to as "F-waves" or "Fib-waves") are then classified by the microcontroller 60 by comparing them to a predefined rate zone limit (e.g. bradycardia, normal, low rate VT, high rate VT, and fibrillation rate zones) and various other characteristics (e.g. sudden onset, stability, physiologic sensors, and morphology, etc.) in order to determine the type of remedial therapy that is needed (e.g. bradycardia pacing, anti-tachycardia pacing, cardioversion shocks or defibrillation shocks, collectively referred to as "tiered therapy").

Cardiac signals are also applied to the inputs of an analog-to-digital (A/D) data acquisition system 90. The data acquisition system 90 is configured to acquire intracardiac electrogram (EGM) signals, convert the raw analog data into digital signals, and store the digital signals for later processing and/or telemetric transmission to an external device 102. The data acquisition system 90 is coupled to the right atrial lead 20, the coronary sinus lead 24, and the right ventricular lead 30 through the switch bank 74 to sample cardiac signals across any pair of desired electrodes.

The microcontroller 60 is further coupled to a memory 94 by a suitable data/address bus 96, wherein the programmable operating parameters used by the microcontroller 60 are stored and modified, as required, in order to customize the operation of the stimulation device 10 to suit the needs of a particular patient. Such operating parameters define, for example, pacing pulse amplitude, pulse duration, electrode polarity, rate, sensitivity, automatic features, arrhythmia detection criteria, and the amplitude, wave shape and vector of each shocking pulse to be delivered to the patient's heart 12 within each respective tier of therapy.

Advantageously, the operating parameters of the stimulation device 10 may be non-invasively programmed into the memory 94 through a telemetry circuit 100 in telemetric communication with the external device 102, such as a programmer, transtelephonic transceiver, or a diagnostic system analyzer. The telemetry circuit 100 is activated by the microcontroller 60 by a control signal 106. The telemetry circuit 100 advantageously allows intracardiac electrograms and status information relating to the operation of the stimulation device 10 (as contained in the microcontroller 60 or memory 94) to be sent to the external device 102 through the established communication link 104.

The stimulation device 10 may further include a physiologic sensor 108, commonly referred to as a "rate-responsive" sensor because it is typically used to adjust pacing stimulation rate according to the exercise state of the patient. However, the physiological sensor 108 may further be used to detect changes in cardiac output, changes in the physiological condition of the heart, or diurnal changes in activity (e.g. detecting sleep and wake states). Accordingly, the microcontroller 60 responds by adjusting the various pacing parameters (such as rate, AV Delay, V-V Delay, etc.) at which the atrial and ventricular pulse generators 70 and 72 generate stimulation pulses.

In accordance with one feature of the present invention, coupling intervals that determine the activation sequence of stimulated chambers or sites, may be adjusted based on changes detected by the physiologic sensor 108. Preferably physiologic sensor 108 includes detection of changes related to the hemodynamic state of the patient and thereby allows adjustment of the coupling intervals to be made in a way that optimizes the hemodynamic response to multisite or multichamber stimulation. One method for accomplishing automatic adjustment of coupling intervals based on physiologic sensor 108 data will be described in detail in conjunction with FIG. 10.

While the physiologic sensor 108 is shown as being included within the stimulation device 10, it is to be understood that the physiologic sensor 108 may alternatively be external to the stimulation device 10, yet still be implanted within, or carried by the patient. A common type of rate responsive sensor is an activity sensor, such as an accelerometer or a piezoelectric crystal, which is mounted within the housing 40 of the stimulation device 10. Other types of physiologic sensors are also known, for example, sensors which sense the oxygen content of blood, cardiac output, respiration rate and/or minute ventilation, pH of blood, ventricular gradient, etc. However, any sensor may be used which is capable of sensing a physiological parameter, which corresponds to the exercise or hemodynamic state of the patient.

The stimulation device 10 additionally includes a power source such as a battery 110 that provides operating power to all the circuits shown in FIG. 2. For the stimulation device 10, which employs shocking therapy, the battery 110 must be capable of operating at low current drains for long periods of time, and also be capable of providing high-current pulses (for capacitor charging) when the patient requires a shock pulse. The battery 110 must preferably have a predictable discharge characteristic so that elective replacement time can be detected. Accordingly, the stimulation device 10 can employ, for example, lithium/silver vanadium oxide batteries.

As further shown in FIG. 2, the stimulation device 10 is shown as having an impedance measuring circuit 112 which is enabled by the microcontroller 60 by a control signal 114. The known uses for an impedance measuring circuit 120 include, but are not limited to, lead impedance surveillance during the acute and chronic phases for assessing the mechanical integrity of the lead; detecting operable electrodes and automatically switching to an operable pair if mechanical disruption occurs in one lead; measuring respiration or minute ventilation; detecting when the device has been implanted; and a variety of hemodynamic variables such as measuring stroke volume; and detecting the opening of the valves, etc. The impedance measuring circuit 120 is advantageously coupled to the switch bank 74 so that any desired electrode may be used.

The impedance measuring circuit 112 may be used advantageously in the present invention for monitoring hemodynamic indicators, such as ventricular impedance as an indication of cardiac output, to provide feedback in the selection of optimal coupling intervals. Impedance measuring circuit 112 may be used alone or in conjunction with physiological sensor 108 for providing such feedback. This data may be periodically stored in memory 94 such that a physician may then access this data during patient follow-up visits to obtain useful information in manually selecting and programming coupling intervals. Preferably, this data may be used by the stimulation device 10 to automatically adjust coupling intervals as will be described in conjunction with FIG. 10.

In cases where a primary function of the stimulation device 10 is to operate as an implant able cardioverter/defibrillator (ICD) device, it must detect the occurrence of an arrhythmia, and automatically apply an appropriate anti-tachycardia pacing (ATP) and/or electrical shock therapy to the heart aimed at terminating the detected arrhythmia. To this end, the microcontroller 60 further controls a shocking circuit 116 by way of a control signal 118. The shocking circuit 116 generates shocking pulses of low (up to 0.5 Joules), moderate (0.5–10 Joules), or high (11 to 40 Joules) energy, as controlled by the microcontroller 60. Such shocking pulses are applied to the patient's heart through at least two shocking electrodes, and as shown in this embodiment, selected from the left atrial coil electrode 28, the RV coil electrode 36, and/or the SVC coil electrode 38 (FIG. 1). As noted earlier, the housing 40 may act as an active electrode in combination with the RV electrode 36, or as part of a split electrical vector using the SVC coil electrode 38 or the left atrial coil electrode 28 (i.e., using the RV electrode as common electrode).

Cardioversion shocks are generally considered to be of low to moderate energy level (so as to minimize pain felt by the patient), and/or synchronized with an R-wave and/or pertaining to the treatment of tachycardia. Defibrillation shocks are generally of moderate to high energy level (i.e., corresponding to thresholds in the range of 5–40 Joules), delivered asynchronously (since R-waves may be too disorganized), and pertaining exclusively to the treatment of fibrillation. Accordingly, the microcontroller 60 is capable of controlling the synchronous or asynchronous delivery of the shocking pulses.

Figure 3:
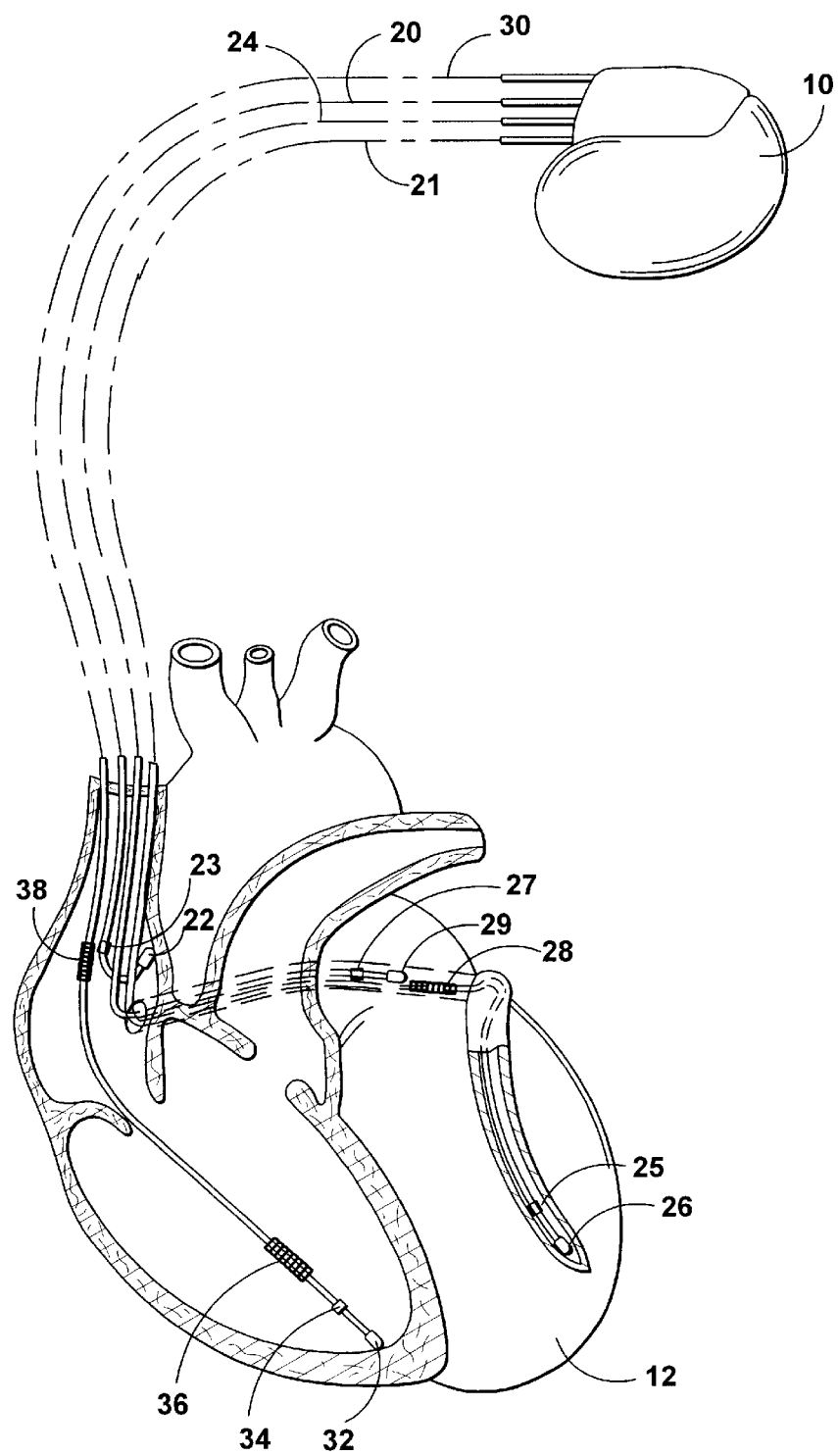
FIG. 3 is a simplified, partly cutaway view illustrating an implant able stimulation device in electrical communication with at least four bipolar leads implanted into a patient's heart representing a preferred embodiment of the present invention.

FIG. 3 illustrates a preferred embodiment of the present invention showing one bipolar lead 20 implanted in the right atrium, one bipolar lead 21 implanted in the coronary sinus region adjacent to left atrium, one bipolar high-voltage lead 30 implanted in the right ventricle, and another bipolar high-voltage lead 31 implanted in the coronary sinus region adjacent to the left ventricle. Using this electrode configuration with the stimulation device 10, independent unipolar or bipolar stimulation and sensing of either or both atria is possible, or, alternatively, combination bi-atrial stimulation or sensing can be performed with the cathode and anode assignments applied to the right atrial tip electrode 22, right atrial ring electrode 23, left atrial ring electrode 27, and left atrial tip electrode 29 as desired.

In addition, independent unipolar or bipolar stimulation and sensing an be provided separately in the right and left ventricles or, alternatively, combination bi-ventricular stimulation or sensing can be performed with the cathode and anode assignments applied to the right ventricular tip electrode 32, right ventricular ring electrode 34, left ventricular ring electrode 25, and left ventricular tip electrode 26 as desired.

Figure 4:
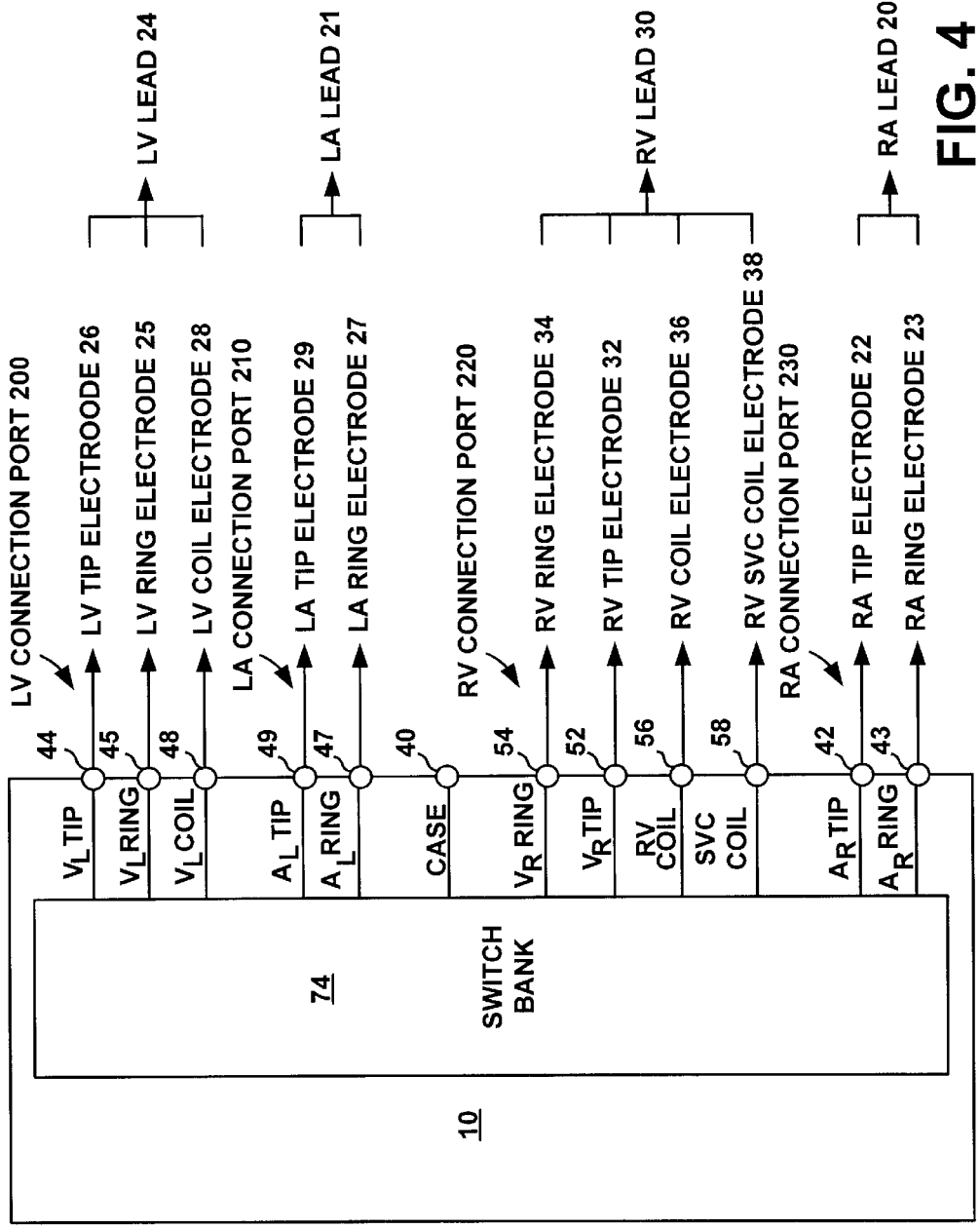
FIG. 4 is a block diagram of the stimulation device of FIG. 3, illustrating a switch with four ports for connection to four leads.

In this embodiment, and as further illustrated in FIG. 4, the stimulation device 10 of FIG. 3 includes four bipolar connection ports 200, 210, 220 and 230. A left ventricular connection port (LV connection port) 200 accommodates the left ventricular lead (LV lead) 24 with terminals 44, 45, 48 that are associated with the left ventricular tip electrode (LV tip electrode) 26, the left ventricular ring electrode (LV ring electrode) 25, and the left atrial coil electrode (LA coil electrode) 28, respectively.

A left atrial connection port (LA connection port) 210 accommodates the left atrial lead (LA lead) 21 with terminals 49, 47 that are associated with the left atrial tip electrode (LA tip electrode) 29 and the left atrial ring electrode (LA ring electrode) 27, respectively. A right ventricular connection port (RV connection port) 220 accommodates the right ventricular lead (RV lead) 30 with terminals 52, 54, 56, 58 that are associated with the right ventricular tip electrode (RV tip electrode) 32, the right ventricular ring electrode (RV ring electrode) 34, the right ventricular coil electrode (RVCE) 36 and the right ventricular SVC coil electrode (RV SVC coil electrode) 38, respectively. A right atrial connection port (RA connection port) 230 accommodates the right atrial lead (RA lead) 20 with terminals that are associated with the right atrial tip electrode (RA tip electrode) 22 and the right atrial ring electrode (RA ring electrode) 23, respectively.

It is recognized that numerous variations exist in which combinations of unipolar, bipolar and/or multipolar leads may be positioned at desired locations within the heart in order to provide multichamber or multisite stimulation. The present invention provides for the flexibility of independent stimulation and/or sensing at multiple sites by providing a cardiac stimulation device that includes multiple connection ports with unique terminals for the electrode(s) associated with each stimulation site as well as independent sensing and output circuitry for each stimulation site. As such, stimulation and sensing sites are not obligatorily coupled together by adapters or hardwiring within the stimulation device that would otherwise preclude independent sensing and stimulation at each pacing site during either multichamber or multisite pacing.

Figure 5:
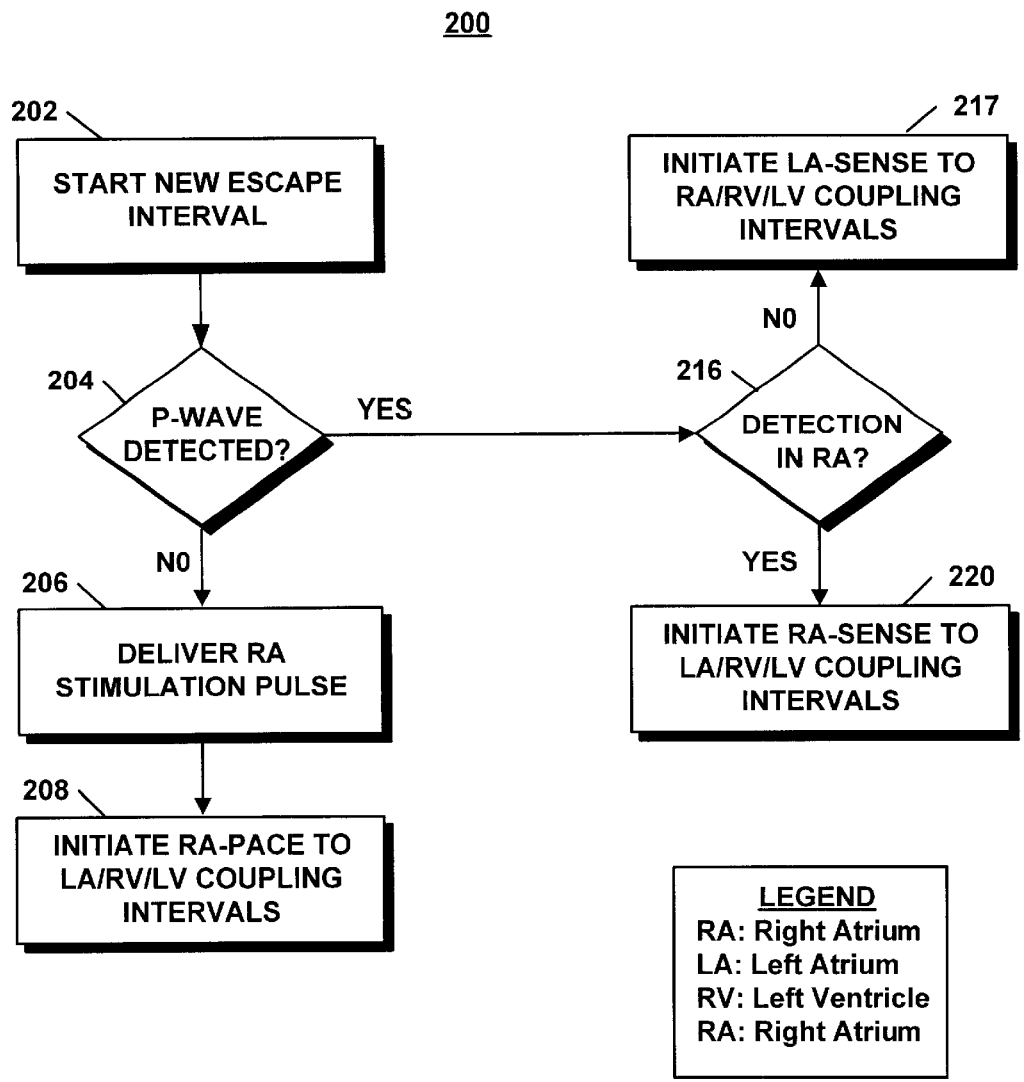
FIG. 5 depicts a flow chart describing an overview of a method for automatically configuring sensing electrodes for use in the cardiac stimulation device of the present invention.
Figure 6:
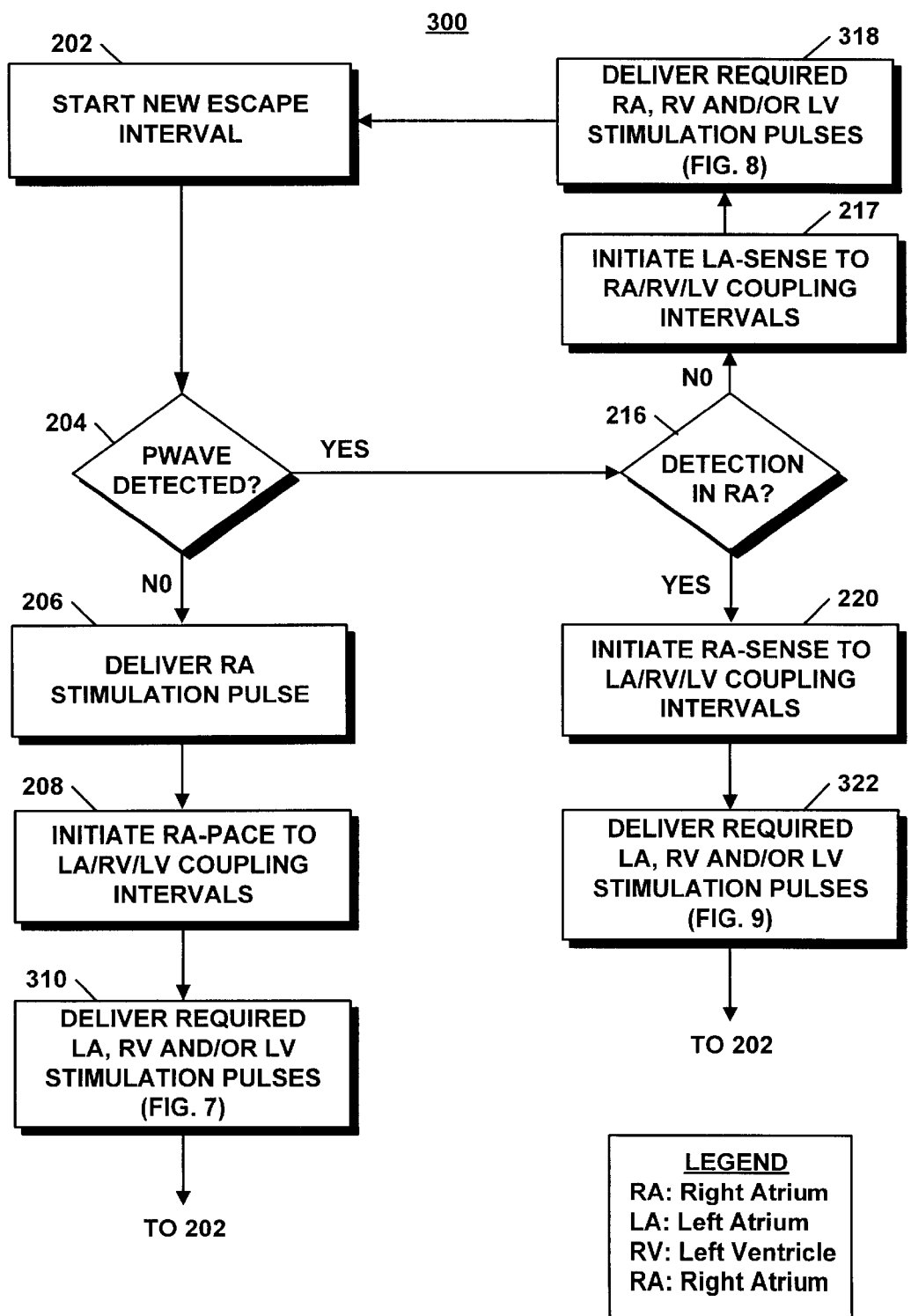
FIGS. 6 through 9 depict flow chart describing a method for automatically configuring stimulation electrodes for use in the cardiac stimulation device of the present invention.

FIGS. 5 and 6 illustrate a flow chart describing methods of operation 200 and 300, respectively, that are implemented in one embodiment of the stimulation device 10 in which defined coupling intervals are applied by microcontroller 60 for controlling the sequence of stimulation pulse delivery by the atrial pulse generator 70 and the ventricular pulse generator 72. In this flow chart, and the other flow charts described herein, the various algorithmic steps are summarized in individual "blocks". Such blocks describe specific actions or decisions that must be made or carried out as the algorithm proceeds. Where a microcontroller (or equivalent) is employed, the flow charts presented herein provide the basis for a "control program" that may be used by such a microcontroller (or equivalent) to effectuate the desired control of the stimulation device. Those skilled in the art may readily write such a control program based on the flow charts and other descriptions presented herein.

The methods 200 and 300 will be described in relation to the implant configuration of FIG. 3, where sensing and pacing are performed in the right atrium, left atrium, right ventricle and left ventricle. It is recognized that the algorithmic steps illustrated in FIGS. 5 and 6 may easily be modified to control the stimulation sequence during any multi-chamber or multi-site stimulation configuration.

At the time of implant, coupling intervals are programmed by the physician to precisely control the activation sequence of all four chambers whenever pacing is required. Default nominal values stored in the stimulation device 10 may also be selected. Coupling intervals are defined in association with paced and sensed events occurring at each stimulation site. For example, the delivery of a right atrial stimulation pulse by the atrial pulse generator 70 will cause microcontroller 60 to initiate three coupling intervals: one associated with the left atrium; another associated with the right ventricle; and yet another associated with the left ventricle. These coupling intervals control the time between the delivery of the right atrial stimulation pulse and the delivery of the left atrial, right ventricular, and left ventricular stimulation pulses, respectively.

Likewise, the detection of a P-wave in the right atrium by the atrial sense circuitry 82 will also cause microcontroller 60 to initiate three coupling intervals associated with the left atrium, right ventricle, and left ventricle. However, these coupling intervals may be different than the coupling intervals initiated due to a right atrial paced event. Similarly, left atrial coupling intervals are defined for the case of a left atrial event being detected before a right atrial event for controlling the time between the left atrial detection and right atrial stimulation, right ventricular stimulation and left ventricular stimulation. In addition, the system can be configured to deliver the left atrial stimulus before the right atrial stimulus, or the left ventricular stimulus before the right ventricular stimulus.

The method 200 and 300 of FIGS. 5 and 6 represent the application of these coupling intervals over one cardiac cycle. It is assumed in this example, that the stimulation device 10 is programmed to operate in a demand mode in the atrial channels and in a triggered mode in the ventricular channels although, it can be set to operate in the triggered mode in both the atrium and ventricle or the triggered mode in the atrium and the demand mode in the ventricle.

Starting at step 202, a new escape interval is initiated. The length of this escape interval is determined by the programmed base pacing (or stimulation) rate. For example, if the base pacing rate is programmed to be 60 beats per minute, then the escape interval is 1000 msec. Method 200 waits for the detection of an intrinsic P-wave by atrial sense circuit 82 prior to expiration of the escape interval.

If at decision step 204 the method 200 determines that the escape interval has expired before an intrinsic P-wave is detected, microprocessor 60 triggers the right atrial output circuitry in the atrial pulse generator 70 to deliver a stimulation pulse to the right atrium at step 206, according to the programmed electrode configuration for stimulation in the right atrium.

Figure 7:
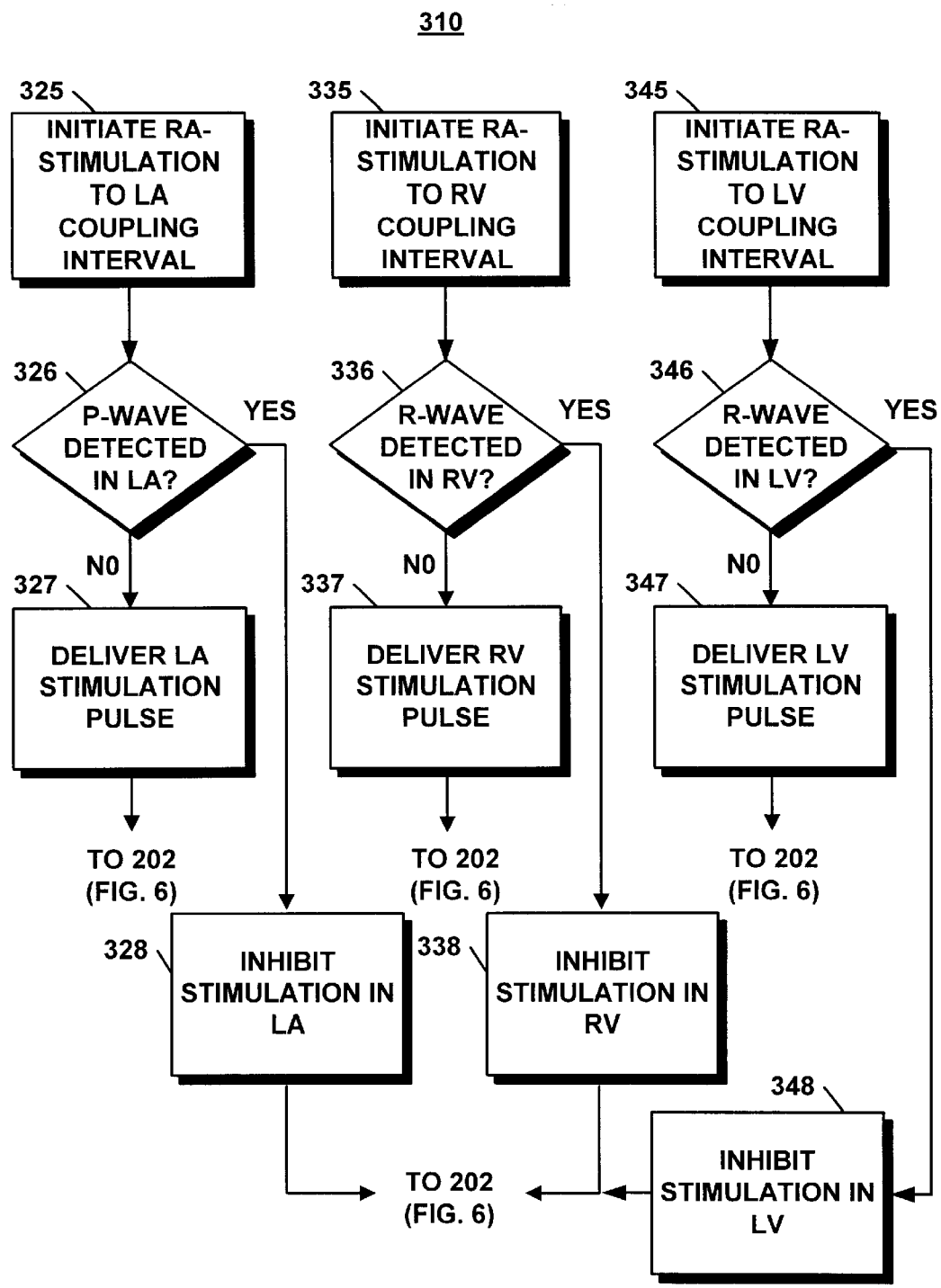

The delivery of a right atrial stimulation pulse causes microprocessor 60 to trigger timing control circuitry 79 to start three separate timers simultaneously at step 208. As it is illustrated in FIG. 7, one timer initiates a right atrial pace to left atrium (RApace to LA) coupling interval at step 325. Another timer initiates a right atrial pace to right ventricle (RApace to RV) coupling interval at step 335. The third timer simultaneously initiates a right atrial pace to left ventricle (RApace to LV) coupling interval at step 345. Upon expiration of the coupling intervals, the stimulation device 10 delivers the required stimulation pulses at step 310.

FIG. 7 illustrates further details of step 310. Upon expiration of the right atrial pace to left atrium (RApace to LA) coupling interval (step 325), method 300 inquires, at decision step 326, if an intrinsic left atrial depolarization (P-wave) is detected. If it is, method 300 inhibits the delivery of a left atrial stimulation pulse at step 328. If an intrinsic left atrial depolarization is not detection at step 326, the microcontroller 60 triggers the left atrial output circuitry of atrial pulse generator 70 to deliver a left atrial (LA) stimulation pulse at step 327.

Similarly, upon expiration of the right atrial pace to left atrium (RApace to RV) coupling interval at step 335, method 300 inquires, at decision step 336, if an intrinsic right ventricular depolarization (R-wave) is detected. If it is, method 300 inhibits the delivery of a right ventricular stimulation pulse at step 338. If an intrinsic right ventricular depolarization is not detection at step 336, the microcontroller 60 triggers the right atrial output circuitry of the ventricular pulse generator 72 to deliver a right ventricular (RV) stimulation pulse at step 337.

In a similar manner, upon expiration of the right atrial pace to left ventricle (RApace to LV) coupling interval at step 345, method 300 inquires, at decision step 346, if an intrinsic left ventricular depolarization (R-wave) is detected. If it is, method 300 inhibits the delivery of a left ventricular stimulation pulse at step 348. If an intrinsic left ventricular depolarization is not detected at step 346, the microprocessor 60 triggers the left atrial output circuitry of the ventricular pulse generator 72 to deliver a left ventricular (LV) stimulation pulse at step 347.

With respect to steps 328, 338, and 348, if a sensed event occurs on the atrial channel or the ventricular channel, method 300 detects the chamber in which the sensed event originated and the times the delivery of the output pulse to the other chamber in accord with the automatic or physician set interval.

After the expiration of all these three coupling intervals and the delivery of triggered stimulation to the designated stimulation sites, method 300 returns to step 202 where the microprocessor 60 initiates a new escape interval to start the next cardiac pacing cycle.

Returning now to FIGS. 5 and 6, if a P-wave is detected by the atrial sense circuitry 82 prior to the expiration of the escape interval at decision step 204, methods 200 and 300 determine, at decision step 216, if this detection has been made by the right atrial sensing circuitry or the left atrial sensing circuitry of the atrial sense circuit 82.

Figure 8:
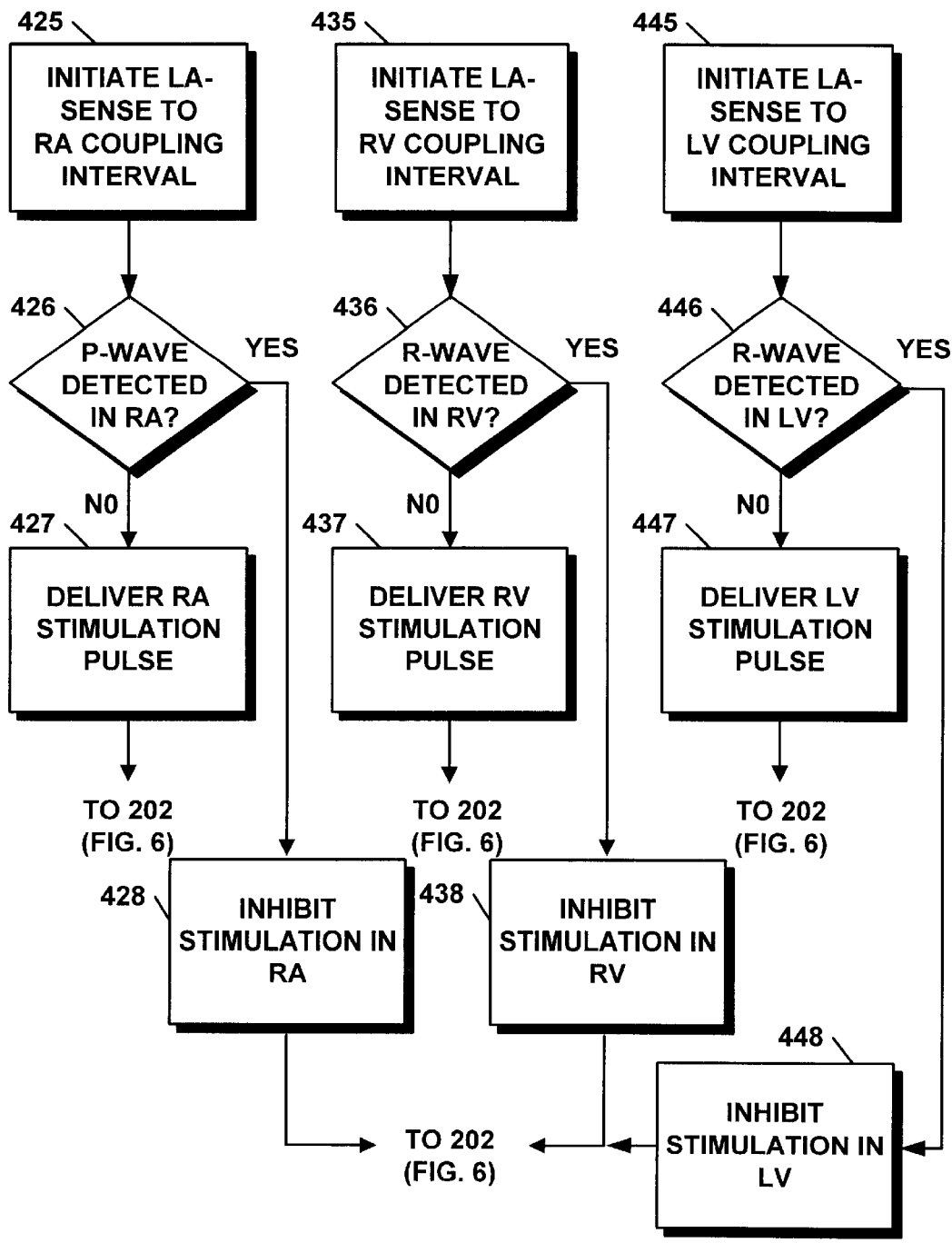

If a P-wave is detected at step 204 and the microprocessor 60 determines that the P-wave has been detected in the left atrial sense circuitry of atrial sense circuitry 82 at decision step 216, then the coupling intervals associated with a left atrial sense event are initiated by timing the control circuitry 79 at step 217. As it is illustrated in FIG. 8, a left atrial sense to right atrial (LAsense to RA) coupling interval is initiated in one timer at step 425. This coupling interval may or may not be equal to the coupling interval between the right and left atria associated with a detected right atrial event.

On a separate timer, the timing control circuitry 79 simultaneously initiates a left atrial sense to right ventricle (LAsense to RV) coupling interval at step 435. Another timer starts the left atrial sense to left ventricle (LAsense to LV) coupling interval at step 445. If a sensed event occurs within the designated coupling intervals, the timing of the stimulus output to the other chamber is based on the sensed event and not the output pulse in the atrium. Upon expiration of the coupling intervals, the stimulation device 10 delivers the required stimulation pulses at step 318.

FIG. 8 illustrates further details of step 318. Upon expiration of the left atrial sense to right atrial (LAsense to RA) coupling interval at step 425, method 300 inquires, at decision step 426, if an intrinsic right atrial depolarization (P-wave) is detected. If it is, method 300 inhibits the delivery of a right atrial stimulation pulse at step 428. If an intrinsic left atrial depolarization is not detection at step 426, the microprocessor 60 triggers the right atrial output circuitry of the atrial pulse generator 70 to deliver a stimulation pulse to the right atrium at step 427.

Similarly, upon expiration of the left atrial to right ventricular (LAsense to RV) coupling interval at step 435, method 300 inquires, at decision step 436, if an intrinsic right ventricular depolarization (R-wave) is detected. If it is, method 300 inhibits the delivery of a right ventricular stimulation pulse at step 438. If an intrinsic right ventricular depolarization is not detection at step 436, the microcontroller 60 triggers right ventricular output circuitry of the ventricular pulse generator 72 to deliver a stimulation pulse to the right ventricle at step 437.

In a similar manner, upon expiration of the left atrial to left ventricular (LAsense to LV) coupling interval at step 445, method 300 inquires, at decision step 446, if an intrinsic left ventricular depolarization (R-wave) is detected. If it is, method 300 inhibits the delivery of a left ventricular stimulation pulse at step 348. If an intrinsic left ventricular depolarization is not detection at step 446, the microprocessor 60 triggers the left ventricular output circuit of the ventricular pulse generator 72 to deliver a stimulation pulse to the left ventricle at step 447.

Figure 9:
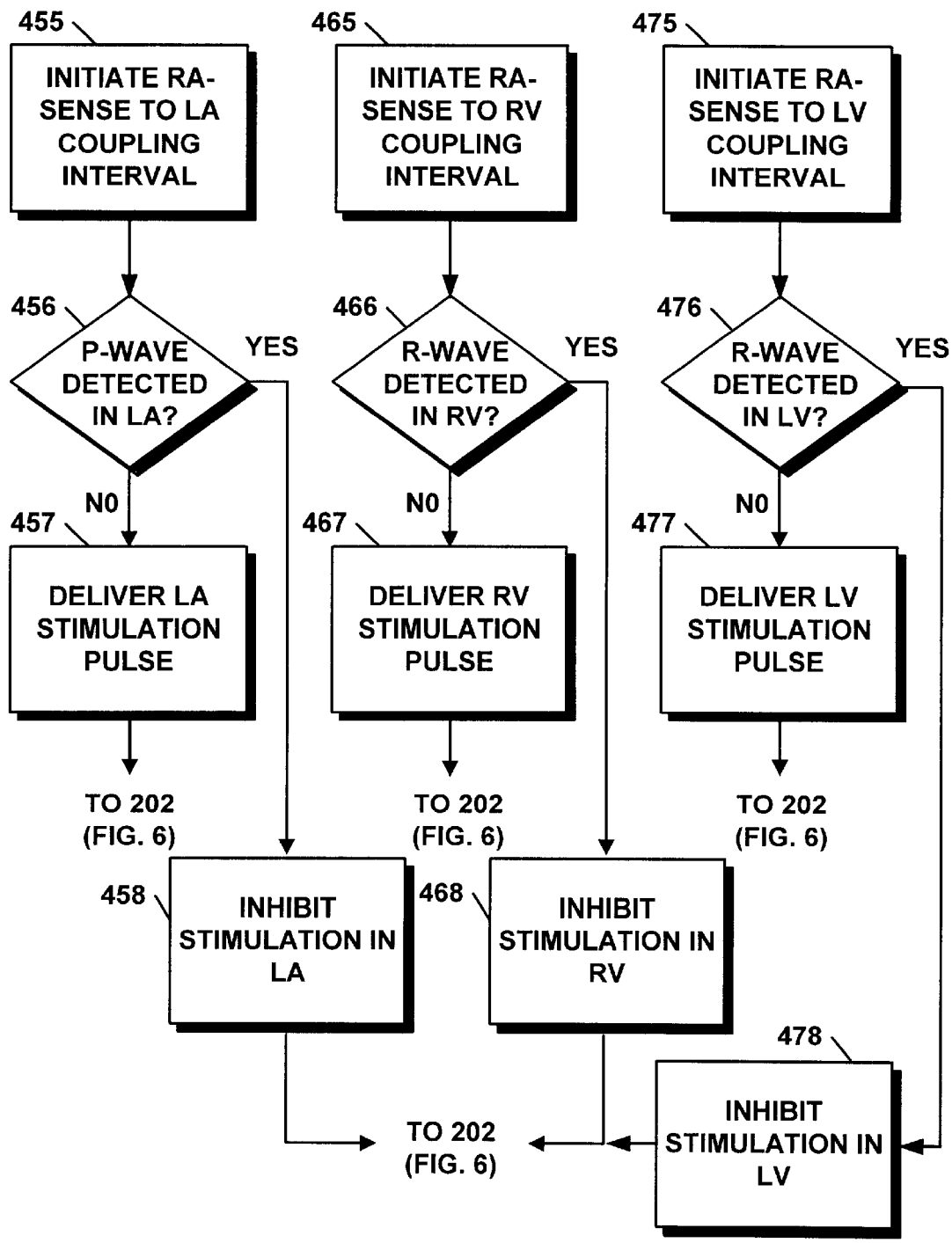

Returning now to FIGS. 5 and 6, if the P-wave detection has been made in the right atrium, the microprocessor 60 commands the timing control circuitry 79 to simultaneously initiate three different timers at step 220. As it is illustrated in FIG. 9, one timer starts the right atrial sense to left atrium (RAsense to LA) coupling interval (step 455). Another timer simultaneously starts the right atrial sense to right ventricle (RAsense to RV) coupling interval (step 465). The third timer starts the right atrial sense to left ventricle (RAsense to LV) coupling interval (step 475). These coupling intervals triggered by a right atrial sense event may be different than the coupling intervals triggered by a right atrial pace event as described above in conjunction with steps 425, 435, and 445. Upon expiration of the coupling intervals, the stimulation device 10 delivers the required stimulation pulses at step 322.

FIG. 9 illustrates further details of step 322. Upon expiration of the right atrial sense to left atrium (RAsense to LA) coupling interval at step 455, method 300 inquires, at decision step 456, if an intrinsic right atrial depolarization (P-wave) is detected. If it is, method 300 inhibits the delivery of a left atrial stimulation pulse at step 457. If an intrinsic left atrial depolarization is not detection at step 456, the microprocessor 60 triggers the left atrial output circuitry of the atrial pulse generator 70 to deliver a left atrial (LA) stimulation pulse at step 457.

Similarly, upon expiration of the right atrial pace to right ventricular (RApace to RV) coupling interval at step 465, method 300 inquires, at decision step 466, if an intrinsic right ventricular depolarization (R-wave) is detected. If it is, method 300 inhibits the delivery of a right ventricular stimulation pulse at step 468. If an intrinsic right ventricular depolarization is not detection at step 436, the microcontroller 60 triggers the ventricular pulse generator 72 to deliver a right ventricular (RV) stimulation pulse at step 467.

In a similar manner, upon expiration of the right atrial sense to left ventricular (RAsense to LV) coupling interval at step 475, method 300 inquires, at decision step 476, if an intrinsic left ventricular depolarization (R-wave) is detected. If it is, method 300 inhibits the delivery of a left ventricular stimulation pulse at step 478. If an intrinsic left ventricular depolarization is not detection at step 476, the microprocessor 60 triggers the left atrial output circuitry of the ventricular pulse generator 72 to deliver a left ventricular (LV) stimulation pulse. After the expiration of these three coupling intervals and the delivery of triggered stimulation to the designated stimulation sites, method 300 returns to step 202 (FIG. 6) where the microprocessor 60 initiates a new escape interval to start the next cardiac cycle.

In this way, the sequential delivery of stimulation pulses to all four chambers of the heart is precisely controlled in order to provide coordinated depolarization of the cardiac chambers. In this example, the stimulation device 10 essentially operates in a demand pacing mode in the right and left atria and in a triggered pacing mode in the right and left ventricles, though other possibilities are similarly feasible, as described herein. Sensing within all of these chambers is still provided, however, in order to accommodate the tachycardia detection features of the stimulation device 10, and to utilize its ability to deliver shocking therapy in addition to pacing therapy as needed.

The programmed settings of the coupling intervals described in conjunction with FIG. 5 are preferably selected in a way that provides optimal hemodynamic benefit to the patient. A medical practitioner may manually program these settings based on clinical measurements of cardiac performance. It is recognized that the selection and programming of numerous coupling intervals associated with numerous stimulation sites could become a time-consuming task. Therefore, the selection of coupling intervals may be semi-automatic or completely automatic. For example, after manual programming of the most critical coupling intervals, the microprocessor 60 might calculate other coupling intervals based on mathematical relationships or patient's history stored in memory 90, or apply default values to other coupling intervals.

In an alternative embodiment of the present invention, the optimal coupling intervals may be selected automatically based on measurements of cardiac function or other physiological parameters that relate to the clinical condition of the patient as measured by physiological sensor 108 and/or impedance measuring circuit 112.

Figure 10:
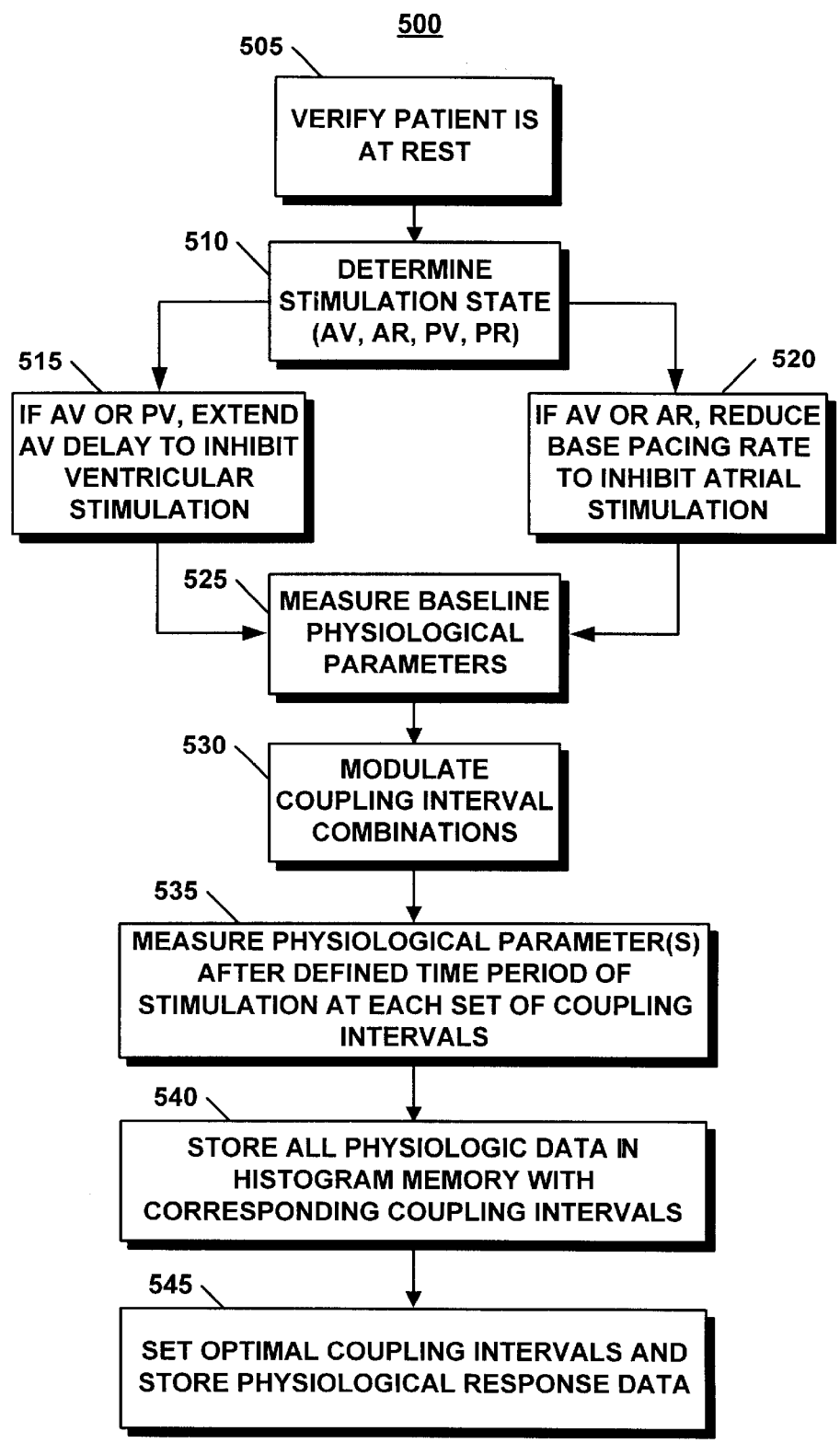
FIG. 10 is a flow chart describing an overview of a method implemented by the stimulation device of FIG. 2, for automatically adjusting the coupling intervals used in the methods of FIGS. 5–9, to achieve an optimal physiological response to a multichamber stimulation therapy.

FIG. 10 illustrates a method 500 for automatically adjusting the coupling intervals. The method 500 may be performed upon delivery of an external command, or on a programmed periodic basis, for example, daily. Method 500 starts at step 505 by verifying that the patient is at rest. Preferably, physiological measurements made for comparing cardiac state during different pacing modalities is performed only at rest in order to avoid confounding variables that may occur if the patient is engaged in varying levels of activity during the test. Various methods may be used to verify resting state, such as heart rate or other physiological sensor 108 measured parameters. For details regarding one method for verifying resting state reference is made to U.S. Pat. No. 5,476,483 to Bornzin.

At step 510, the microprocessor 60 determines the present pacing state of the stimulation device 10. If the device 10 is programmed to be operating in a demand mode in both the atrial and ventricular chambers, it may be in one of four pacing states: atrial pacing and ventricular pacing (AV pacing state), atrial pacing and ventricular sensing (AR pacing state), atrial sensing and ventricular pacing (PV pacing state) or atrial sensing and ventricular sensing (PR pacing state).

If the stimulation device 10 is pacing in the ventricle, that is in either the AV or PV pacing states, an attempt is made to inhibit ventricular pacing by extending the atrial-ventricular (AV) delay to allow more time for an intrinsic R-wave to occur at step 515. If the stimulation device 10 is pacing in the atrium, that is in either the AV or AR pacing states, an attempt is made to inhibit atrial pacing by reducing the base pacing rate in order to allow the natural heart rate to predominate at step 520.

Preferably, all pacing is inhibited in order to obtain a baseline physiologic measurement during the natural resting state of the heart. If ventricular pacing cannot be inhibited, even at the maximum AV delay setting, such as in the situation of total AV block, no further attempt is made to inhibit ventricular pacing. Atrial pacing may also not be inhibited even at a minimum pacing rate due to sinus node dysfunction with either too slow a native sinus rate or an unstable native sinus rate. In such cases, the minimum base pacing rate and a nominal AV delay are applied.

At step 525, a measurement is made using the physiological sensor 108 and/or impedance measurement circuit 112 to establish a baseline cardiac function. At step 530, the coupling intervals are modulated in a way that allows testing of numerous combinations of coupling intervals, thus altering the activation sequence, in order to determine the activation sequence and timing that allows optimal improvement in cardiac state. Initially, coupling intervals between the atria and coupling intervals between the ventricles may be modulated. Next, the AV delay, herein referred to as the atrial to ventricular coupling intervals, may be modulated. Pacing should be sustained for any given set of "test" coupling intervals for a defined minimum time period, such as one minute, to allow the functional state of the heart to stabilize under the "test" conditions before making physiological measurements at step 535.

Preferably, the stimulation device 10 operates in a trigger mode throughout this test in order to provide a steady cardiac rhythm at each set of coupling intervals. The physiological measurement made by the sensor 108 and/or the impedance measurement made by impedance measuring circuit 112 are stored in memory 94 (FIG. 2) with codes indicating the corresponding coupling interval settings at step 540.

The coupling interval settings resulting in the greatest improvement in cardiac function based on sensor 108 measurements and/or impedance circuit 112 measurements are selected as the final settings. At step 545, the optimal coupling interval settings are automatically re-programmed. The physiologic sensor 108 measurement and/or the impedance measuring circuit 112 measurement at these final settings should be stored in histogram memory 94 to be recalled and displayed graphically over time during patient follow-up visits.

Thus, a multichamber or multisite cardiac stimulation device has been provided which allows independent sensing and stimulation at multiple sites within the heart according to programmed electrode configurations. Furthermore, a method by which the activation sequence of the stimulated-sites may be precisely controlled using programmable coupling intervals has been provided. Thus, greater flexibility in sensing and stimulation during multisite or multichamber stimulation therapies may be achieved whereby pacing therapies may be individually tailored to patient need so that optimal hemodynamic or electrophysiological results may be realized.

While detailed descriptions of specific embodiments of the present invention have been provided, it would be apparent to those reasonably skilled in the art that numerous variations of multi-site or multi-chamber stimulation configurations are possible in which the concepts and methods of the present invention may readily be applied. The descriptions provided herein, therefore, are for the sake of illustration and are no way intended to be limiting.

What is claimed is:

1. A method of automatically controlling an activation sequence of a plurality of electrodes that are positioned in multiple cardiac chambers, for use with a multi-site cardiac stimulation device, the method comprising the steps of:
   defining a plurality of electrode configurations corresponding to available activation sequences of the electrodes;
   selectively delivering a stimulus, on demand, to a cardiac chamber;
   sensing a cardiac event in the cardiac chamber by using a first electrode configuration;
   initiating a coupling interval for the multiple cardiac chambers;
   controlling the activation sequence of the electrodes by selecting an electrode configuration based on the cardiac chamber in which the cardiac event is sensed or a stimulus delivered;
   automatically acquiring a measurement of the cardiac event using the electrode configuration; and
   automatically adjusting the coupling interval in response to the measurement of the cardiac event.

2. The method according to claim 1, wherein the sensing step includes sensing intrinsic depolarizations in at least two cardiac chambers.

3. The method according to claim 2, wherein the step of delivering a stimulus includes stimulating at least two cardiac chambers.

4. The method according to claim 3, further including the step of determining an inter-atrial conduction (A-A) delay by selecting a coupling interval defined according to whether an intrinsic atrial depolarization is first sensed in a right atrium or in a left atrium.

5. The method according to claim 4, wherein the step of automatically adjusting includes selecting a right-to-left atrial coupling interval to control an interval between an intrinsic right atrial depolarization (P-wave) and a delivery of a left atrial stimulus.

6. The method according to claim 4, wherein the step of automatically adjusting includes selecting a left-to-right atrial coupling interval to control an interval between an intrinsic left atrial depolarization (P-wave) and a delivery of a right atrial stimulus.

7. The method according to claim 1, wherein the step of automatically adjusting further includes adjusting the coupling interval based on a stimulation event in any one of the multiple cardiac chambers.

8. The method according to claim 1, wherein the step of initiating a coupling interval includes initiating a unique coupling interval for a stimulation site, between the stimulation site and remaining stimulation sites, in terms of any one or more of: a stimulations event or an intrinsic depolarization occurring at the stimulation site.

9. The method according to claim 1, further including sensing an occurrence of an intrinsic atrial depolarization in any one or more of a left atrium or a right atrium.

10. The method according to claim 9, further including delivering a right atrial stimulation pulse when no intrinsic atrial depolarization is sensed.

11. The method according to claim 10, wherein the step of initiating the coupling interval includes initiating one or more coupling intervals from the right atrial stimulation pulse to any one or more of: a left atrial stimulation pulse, a right ventricular stimulation pulse, or a left ventricular stimulation pulse.

12. The method according to claim 10, further including detecting an occurrence of an intrinsic right atrial depolarization.

13. The method according to claim 12, wherein when the intrinsic right atrial depolarization is not sensed, initiating one or more coupling intervals from the intrinsic right atrial depolarization to any one or more of: a left atrial stimulation pulse, a right ventricular stimulation pulse, or a left ventricular stimulation pulse.

14. The method according to claim 13, wherein when an intrinsic left atrial depolarization is sensed, initiating one or more coupling intervals from the intrinsic left atrial depolarization to any one or more of: a right atrial stimulation pulse, a right ventricular stimulation pulse, or a left ventricular stimulation pulse.

15. The method according to claim 1, further including automatically selecting a sensing polarity for each sensing site in the multiple cardiac chambers.

16. The method according to claim 15, wherein the step of automatically selecting the sensing polarity includes designating any of an anode or a cathode assignment to at least one of the plurality of sensing electrodes.

17. The method according to claim 16, wherein the step of designating includes selecting a left ventricular tip electrode as the cathode, and further selecting a right ventricular tip electrode as the anode.

18. The method according to claim 16, wherein the step of designating includes selecting a right ventricular tip electrode as the cathode, and further selecting a left ventricular tip electrode as the anode.

19. The method according to claim 16, wherein the step of designating includes assigning any of an anodal sensing or a cathodal sensing to at least one of the plurality of sensing electrodes.

20. The method according to claim 16, wherein the step of designating includes assigning any of an anodal sensing or a cathodal sensing to at least one of the plurality of sensing electrodes.

21. The method according to claim 16, further including automatically selecting a stimulation polarity for each stimulation site in the multiple cardiac chambers.

22. The method according to claim 21, wherein the step of automatically selecting the stimulation polarity includes designating any of an anode or a cathode assignment to at least one of a plurality of stimulation electrodes.

23. The method according to claim 22, wherein the step of designating includes selecting a left ventricular tip electrode as the cathode, and further selecting a right ventricular tip electrode as the anode.

24. The method according to claim 22, wherein the step of designating includes selecting a right ventricular tip electrode as the cathode, and further selecting a left ventricular tip electrode as the anode.

25. The method according to claim 22, wherein the step of designating includes assigning any of an anodal sensing or a cathodal sensing to at least one of the plurality of sensing electrodes.

26. The method according to claim 1, further including allowing intrinsic depolarizations occurring at each stimulation site to be sensed independently.

27. The method according to claim 1, wherein the step of automatically adjusting the coupling interval includes determining a current stimulation state of the stimulation device;
   when the stimulation device is stimulating a ventricle, attempting to inhibit ventricular stimulation by extending an atrial-ventricular (AV) delay;
   when the stimulation device is stimulating an atrium, attempting to inhibit atrial pacing by reducing a base pacing rate;
   measuring one or more baseline physiological parameters; and
   modulating one or more combinations of the coupling intervals for altering the activation sequence so as to determine an activation sequence that allows optimal improvement in the current stimulation state.

28. A multi-site cardiac stimulation device capable of automatically controlling an activation sequence of a plurality of electrodes that are positioned in multiple cardiac chambers, comprising:
   a discriminator, coupled to the plurality of electrodes, that senses a cardiac signal in each of the cardiac chambers, and that identifies a cardiac chamber of origin in which the cardiac signal originates;
   a pulse generator, connected to the electrodes, to selectively deliver stimulation pulses on demand to the cardiac chambers; and
   timing control circuitry, connected to the electrodes, the pulse generator, and the discriminator to initiate coupling intervals for the multiple cardiac chambers based on the cardiac chamber of origin in which an intrinsic depolarization is sensed or a stimulus is delivered, for controlling a timing of the activation sequence, and the timing control circuitry further automatically adjusting the coupling intervals based on measurements acquired by the discriminator.

29. The stimulation device according to claim 28, wherein the discriminator senses an occurrence of an intrinsic atrial depolarization in any one or more of a left atrium or a right atrium.

30. The stimulation device according to claim 29, wherein the pulse generator delivers a right atrial stimulation pulse in the absence of an intrinsic atrial depolarization.

31. The stimulation device according to claim 30, wherein the plurality of electrodes include stimulation electrodes; and
   further including a switch bank that automatically selects polarities for the plurality of stimulation electrodes.

32. The stimulation device according to claim 30, further including a multi-port connector for connection to any one or more of uni-polar, bi-polar, or multi-polar leads.

33. The stimulation device according to claim 32, wherein the multi-port connector includes four bipolar connection ports:
   a left ventricular connection port that couples to a left ventricular lead with terminals associated with a ventricular tip electrode, a left ventricular ring electrode, and a left atrial coil electrode;
   a left atrial connection port that couples to a left atrial lead with terminals associated with a left atrial tip electrode and a left atrial ring electrode;
   a right ventricular connection port that couples to a right ventricular lead with terminals associated with a right ventricular tip electrode, a right ventricular ring electrode, a right ventricular shocking coil, and a right ventricular coil electrode; and
   a right atrial connection port that couples to a right atrial lead with terminals associated with a right atrial tip electrode and a right atrial ring electrode.

34. The stimulation device according to claim 29, wherein the timing control circuitry initiates one or more coupling intervals from a right atrial stimulation pulse to any one or more of: a left atrial stimulation pulse, a right ventricular stimulation pulse, or a left ventricular stimulation pulse.

35. The stimulation device according to claim 29, wherein the sensing circuitry is adapted to further sense an occurrence of an intrinsic right atrial depolarization; and
   wherein in the absence of an intrinsic right atrial depolarization, the timing control circuitry initiates one or more coupling intervals from the intrinsic right atrial depolarization to any one or more of: a left atrial stimulation pulse, a right ventricular stimulation pulse, or a left ventricular stimulation pulse.

36. The stimulation device according to claim 29, wherein in the presence of an intrinsic left atrial depolarization, the sensing circuitry initiates one or more coupling intervals from the intrinsic left atrial depolarization to any one or more of: a right atrial stimulation pulse, a right ventricular stimulation pulse, or a left ventricular stimulation pulse.

37. The stimulation device according to claim 28, wherein the plurality of electrodes include sensing electrodes; and
   further including a switch bank that automatically selects polarities for the plurality of sensing electrodes.

38. A multi-site cardiac stimulation device capable of automatically controlling an activation sequence of a plurality of electrodes that are positioned in multiple cardiac chambers, comprising:
   means for sensing a cardiac signal in each of the multiple cardiac chambers;
   means for detecting a cardiac chamber of origin in which the cardiac signal originates;
   means for selectively generating stimulation energy, on demand, to the multiple cardiac chambers; and
   means for initiating coupling intervals for the multiple cardiac chambers based on the cardiac chamber of origin in which an intrinsic depolarization is sensed or a stimulus is delivered, for controlling a timing of the activation sequence, and for automatically adjusting the coupling intervals based on measurements acquired by the sensing means.

39. The stimulation device according to claim 38, wherein the sensing means senses an occurrence of an intrinsic atrial depolarization in any one or more of a left atrium or a right atrium.

40. The stimulation device according to claim 39, wherein the means for generating stimulation energy delivers a right atrial stimulation pulse in the absence of an intrinsic atrial depolarization;

wherein the initiating means initiates one or more coupling intervals from a right atrial stimulation pulse to any one or more of: a left atrial stimulation pulse, a right ventricular stimulation pulse, or a left ventricular stimulation pulse;

wherein in the absence of an intrinsic right atrial depolarization, the initiating means initiates one or more coupling intervals from the intrinsic right atrial depolarization to any one or more of: a left atrial stimulation pulse, a right ventricular stimulation pulse, or a left ventricular stimulation pulse; and wherein in the presence of an intrinsic left atrial depolarization, the initiating means initiates one or more coupling intervals from the intrinsic left atrial depolarization to any one or more of: a right atrial stimulation pulse, a right ventricular stimulation pulse, or a left ventricular stimulation pulse.

41. The stimulation device according to claim 38, wherein the plurality of electrodes include sensing electrodes; and further including switching means for automatically selecting polarities for the plurality of sensing electrodes.

42. The stimulation device according to claim 38, wherein the plurality of electrodes include stimulation electrodes; and further including switching means for automatically selecting polarities for the plurality of stimulation electrodes.

43. The stimulation device according to claim 38, further including a multi-port connecting means for connection to any one or more of uni-polar, bi-polar, or multi-polar leads; and wherein the multi-port connecting means includes four bipolar connection ports:

a left ventricular connection port that couples to a left ventricular lead with terminals associated with a ventricular tip electrode, a left ventricular ring electrode, and a left atrial coil electrode;

a left atrial connection port that couples to a left atrial lead with terminals associated with a left atrial tip electrode and a left atrial ring electrode;

a right ventricular connection port that couples to a right ventricular lead with terminals associated with a right ventricular tip electrode, a right ventricular ring electrode, a right ventricular shocking coil, and a right ventricular coil electrode; and a right atrial connection port that couples to a right atrial lead with terminals associated with a right atrial tip electrode and a right atrial ring electrode.

* * * * *